United States Patent [19]

Wilson et al.

[11] Patent Number: 4,960,754
[45] Date of Patent: Oct. 2, 1990

[54] 3,7-DIMETHYL-6,7-DIOXO-1,3-OCTADIENE DERIVATIVES AND ORGANOLEPTIC USES THEREOF

[75] Inventors: Richard A. Wilson, Westfield; Michael J. Zampino, Roselle Park; Braja D. Mookherjee, Holmdel; Robert W. Trenkle, Brielle; Anton Van Ouwerkerk, Livingston; Myrna L. Hagedorn, Edison; Michael G. Monteleone, Lyndhurst, all of N.J.

[73] Assignee: International Flavors & Fragrances Inc., New York, N.Y.

[21] Appl. No.: 447,848

[22] Filed: Dec. 8, 1989

Related U.S. Application Data

[63] Continuation-in-part of Ser. No. 2,017, Jan. 9, 1987, abandoned.

[51] Int. Cl.$^5$ ............................................... A61K 7/46
[52] U.S. Cl. ...................................... 512/25; 568/415; 568/675; 568/857; 568/867; 512/27
[58] Field of Search ................... 512/25, 27; 568/415, 568/675, 857, 867

[56] References Cited

U.S. PATENT DOCUMENTS

| | | | |
|---|---|---|---|
| 4,465,869 | 8/1984 | Takaishi et al. | 568/675 |
| 4,762,954 | 8/1988 | Siegmeier et al. | 568/867 |
| 4,814,322 | 3/1989 | Exner et al. | 512/25 |

FOREIGN PATENT DOCUMENTS

| | | | |
|---|---|---|---|
| 0104602 | 4/1984 | European Pat. Off. | 512/25 |

OTHER PUBLICATIONS

Arctander; "Perfume and Flavor Materials of Natural Origin", 1960, published by the Author, Elizabeth, NJ, columns 399 and 400, Covering "Marigold Absolute" (front title page and cols. 399 and 400 attached).

Merchant et al., "Uncatalysed Cleavage of Epoxides", Indian J. Chem., vol. 14B, Jun. 1976, pp. 460 and 461.

Tsankova and Bohlmann, "A Monoterpene from *Aster bakeranus*", *Phytochemistry*, vol. 22, No. 5, pp. 1285–1286, 1983.

*Primary Examiner*—James H. Reamer
*Attorney, Agent, or Firm*—Arthur L. Liberman

[57] ABSTRACT

Described are 3,7-dimethyl-6,7-dioxo-1,3-octadienes or mixtures of same defined according to the structure:

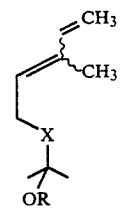

wherein R is hydrogen or ethyl and X is one of the moieties:

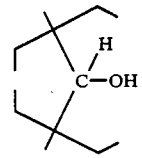

or

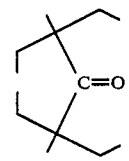

and wherein the wavy lines represent a "E" or "Z" configuration of the methyl and vinyl moiety about the 3,4-pi-bond of the molecule, as well as methods for methods for augmenting or enhancing the aroma of consumable materials including perfumes, colognes and perfumed articles by adding thereto an aroma augmenting or enhancing quantity of at least one of said 3,7-dimethyl-6,7-dioxo-1,3-octadienes.

6 Claims, 23 Drawing Sheets

FIG.1 GLC PROFILE FOR EXAMPLE I

GLC PROFILE FOR EXAMPLE II. CRUDE

GLC PROFILE FOR EXAMPLE II.

FIG. 4 NMR SPECTRUM FOR EXAMPLE II, PEAK 31 OF FIG. 1

NMR SPECTRUM FOR EXAMPLE II, PEAK 32 FIG. 3

FIG.6 NMR SPECTRUM FOR EXAMPLE II, PEAK 33 OF FIG.3.

NMR SPECTRUM FOR EXAMPLE II, PEAK 34 OF FIG. 3.

FIG. 8 NMR SPECTRUM FOR EXAMPLE II, PEAK 26 OF FIG. 2.

GLC PROFILE FOR EXAMPLE III.

GLC PROFILE FOR EXAMPLE II.
DISTILLATION FRACTION II.

NMR SPECTRUM FOR EXAMPLE III, FRACTION II.

NMR SPECTRUM FOR EXAMPLE III, ACETYLATED FRACTION II.

GLC PROFILE FOR EXAMPLE IV.
CRUDE

GLC PROFILE FOR EXAMPLE Ⅴ (A).
CRUDE

GLC PROFILE FOR EXAMPLE V(B).
CRUDE

FIG.16 NMR SPECTRUM FOR EXAMPLE V(B), FRACTION 4.

GLC PROFILE FOR EXAMPLE VI.
CRUDE

NMR SPECTRUM FOR EXAMPLE VI, PEAKS 172 & 174 OF FIG. 17.

GLC PROFILE FOR EXAMPLE VII.

GLC PROFILE FOR EXAMPLE VIII.

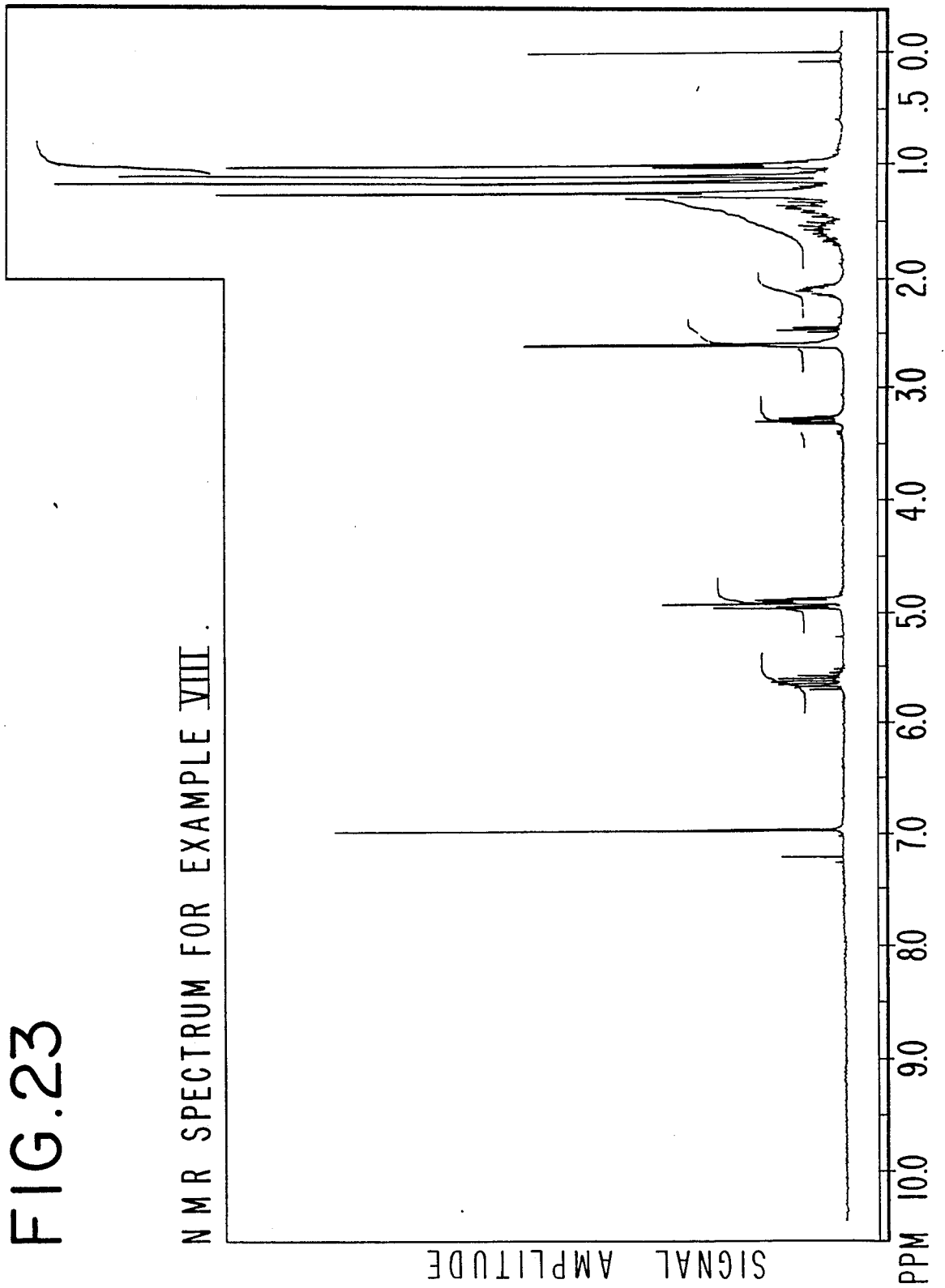
FIG. 23 — NMR SPECTRUM FOR EXAMPLE VIII.

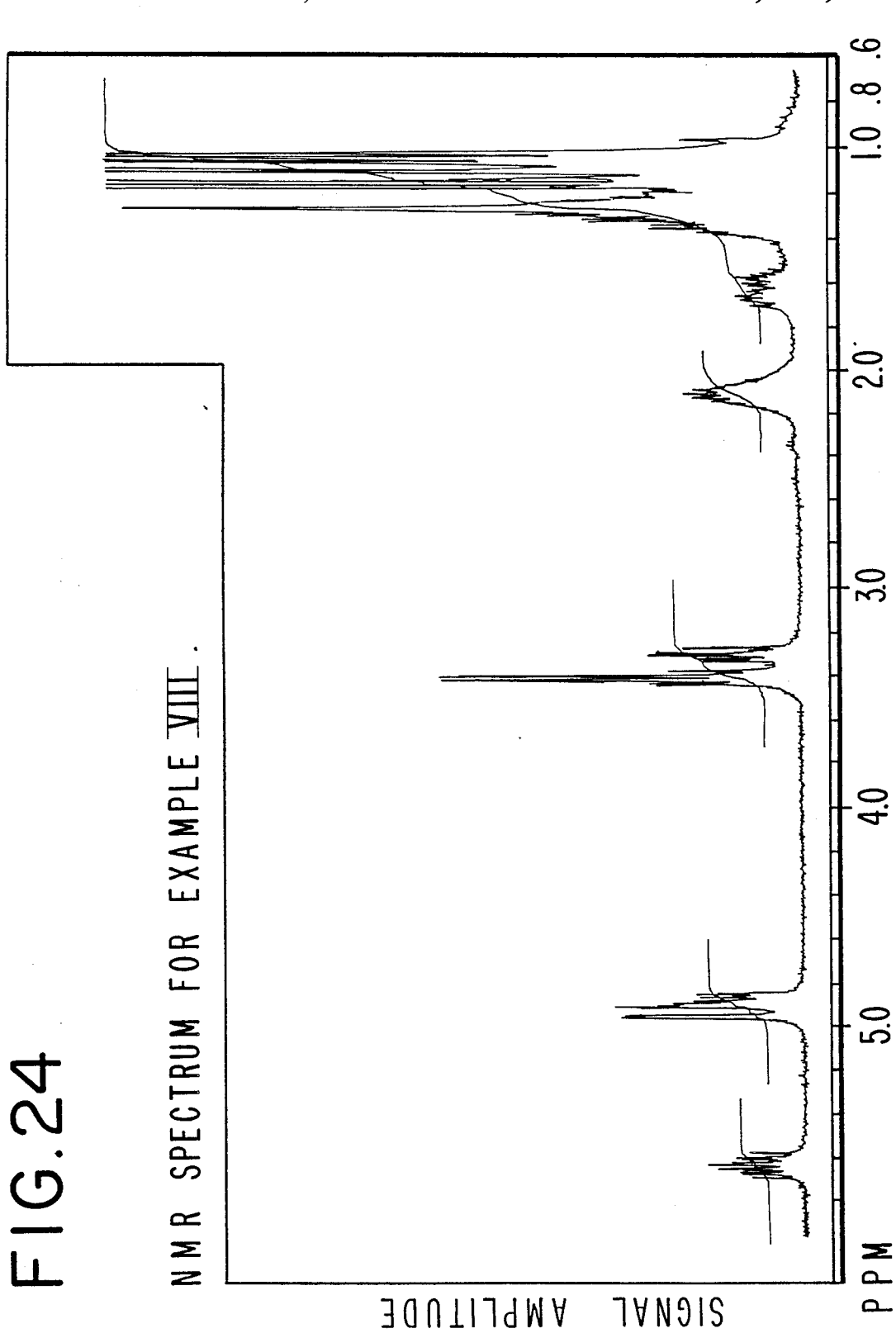
FIG. 24 NMR SPECTRUM FOR EXAMPLE VIII.

3,7-DIMETHYL-6,7-DIOXO-1,3-OCTADIENE DERIVATIVES AND ORGANOLEPTIC USES THEREOF

This application is a continuation-in-part of application for U.S. patent Ser. No. 002,017 filed on Jan. 9, 1987 now abandoned.

BACKGROUND OF THE INVENTION

The instant invention provides 3,7-dimethyl-6,7-dioxo-1,3-octadienes defined according to the generic structure:

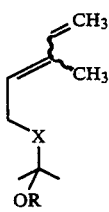

wherein R represents hydrogen or ethyl; wherein X represents one of the moieites:

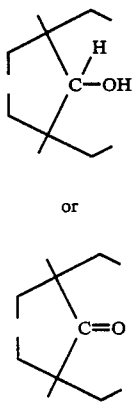

and wherein the wavy lines represent a "E" or "Z" configuration of the methyl and vinyl moiety about the 3,4 double bond of the molecule, as well as the uses thereof for augmenting or enhancing the aroma of perfume compositions, colognes and perfumed articles.

Inexpensive chemical compositions of matter which can provide intense and highly substantive herbaceous, cut geranium stem, floral, fresh fruity, natural green and leafy aromas with floral and citrusy topnotes and fruity, melony, peppery and citrusy undertones are highly desirable in the art of perfumery. Many of the natural materials which provide such fragrances and contribute desired nuances to perfumery compositions as well as perfumed articles including solid or liquid anionic, cationic, nonionic or zwitterionic detergents, perfumed polymers, fabric softener compositions, fabric softener articles, hair preparations, cosmetic powders and the like are high in cost, vary in quality from one batch to another and/or are generally subject to the usual variations of natural products.

Indeed, marigold absolute has been found by us to contain very small quantities of the compounds having the structures:

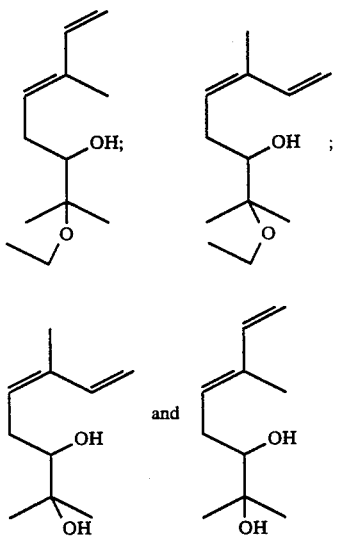

However, these components of marigold absolute have unexpected, unobvious and advantageous perfumery properties with respect to intensity and substantivity when compared with marigold absolute itself.

Arctander, "Perfume and Flavor Materials of Natural Origin", 1960, published by the author discloses at page 399:

Marigold Absolute.

Also called Calendula absolute, Marigold Absolute is extracted from the ligulate florets of *Calendula Officinalis*, known as "Marigold", "Marybud" or "Hollygold" in the United States of America. There is, however, some confusion with respect to the term "marigold" since it has been applied to various other plants of the Compositae family, e.g. Tagetes, etc. Tagetes will be described under its proper name.

The calendula absolute from the true calendula officinalis is probably produced only in France, but it is sold in English speaking countries under the name of Marigold.

The absolute is a very dark greenish-brown, very viscous liquid of an intensely bitter-herbaceous odor. Little is known about its constituents, but as a perfumery material, it has certain interesting and unique notes. Since the plant grows commonly all over Europe, cultivated in the northern part, an increased production could easily be effected.

Its very peculiar note and intense color, however, limits the use of "marigold" to fancy perfume types, modern aldehydic-herbaceous types where the green "crushed-stalk" note may be called for. Marigold Absolute introduces certain natural notes in chrysanthemum fragrances, and it gives interesting effects with oakmoss, mate extract, tea leaf extract, cypriol, iso cyclo citral, etc. Traces of the absolute can be useful in hyacinth, lilac, gardenia, reseda, moss-bases, etc.

See also Tagetes, under which *Tagetes Glandulifera* is discussed, and *Tagetes Patula* under which heading the Indian "genda" is mentioned.

Tsankova and Bohlmann, "A Monoterpene From *Aster Bakeranus*", Phytochemistry, Volume 22, No. 5, pages 1285–1286, 1983 discloses that the compound having the structure:

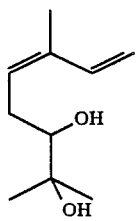

is present in the South African species, *Aster bakeranus* Burtt, Davy ex. C. A. Smith.

Merchant, et al, Indian J. Chem., Volume 14B, Jun. 1976, at pages 460 and 461 discloses the saturated ether derivative having the structure:

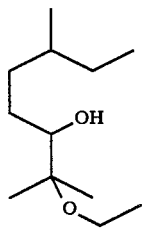

and the synthesis thereof.

Nothing in the prior art, however, discloses the organoleptic properties and particularly the perfume utilities of the 3,7-dimethyl-6,7-dioxo-1,3-octadienes of our invention; and, indeed, nothing in the prior art discloses the compound having the structure:

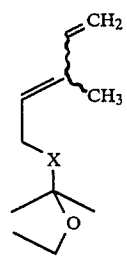

wherein X is one of the moieties:

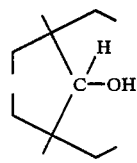

or

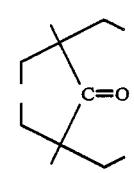

and wherein the wavy lines represent the "E" or "Z" configuration of the vinyl and methyl moiety about the 3,4-pi-bond.

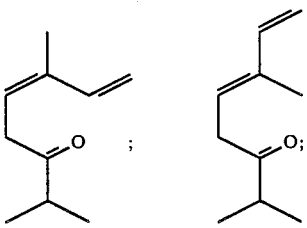

and

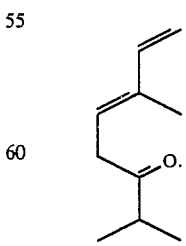

Figure 3:
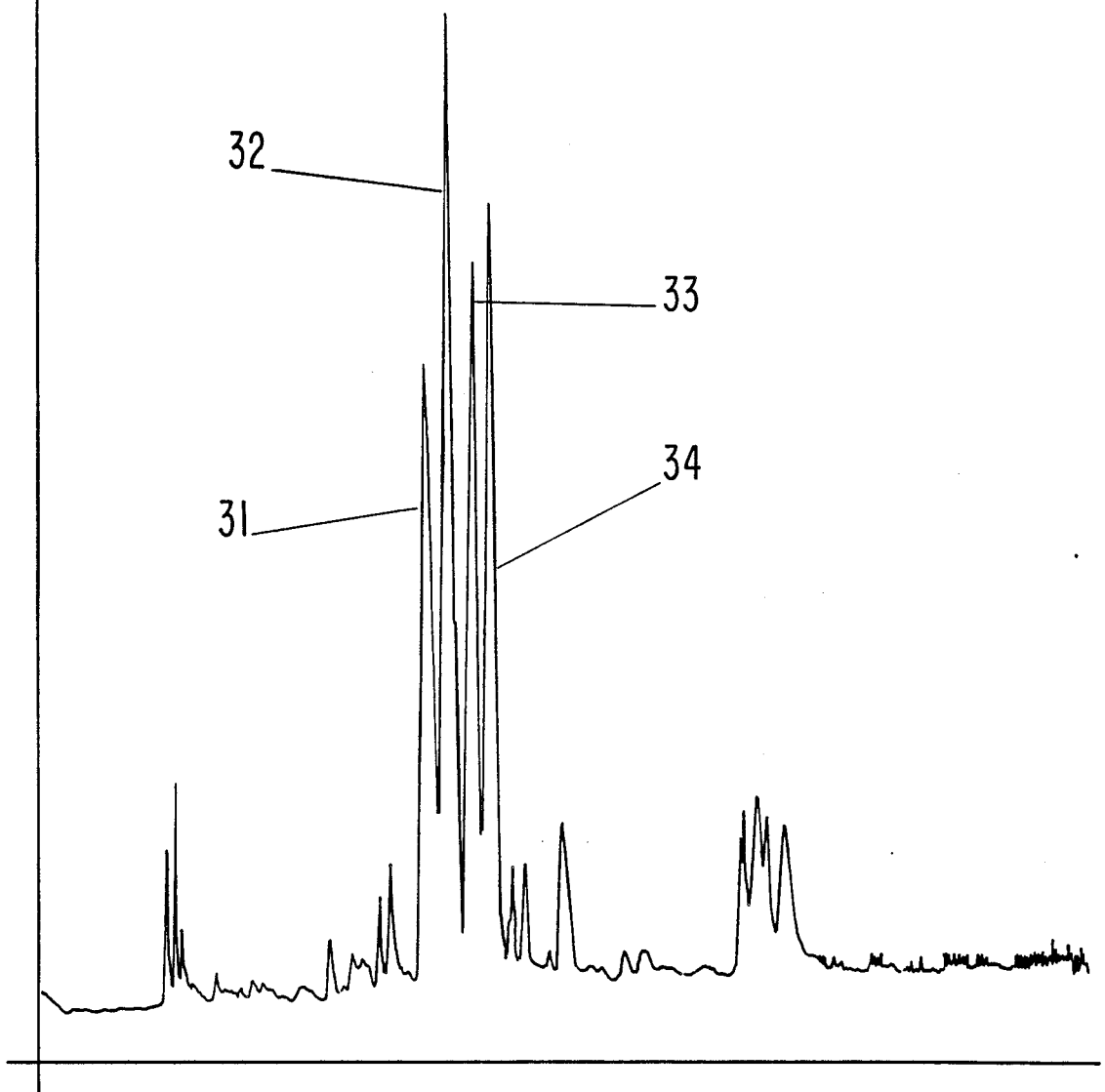
FIG. 3 is the GLC profile for distillation fraction 2 of Example II (Conditions: OV-1 column programmed at 80°–220° C. at 4° C. per minute).
Figure 5:
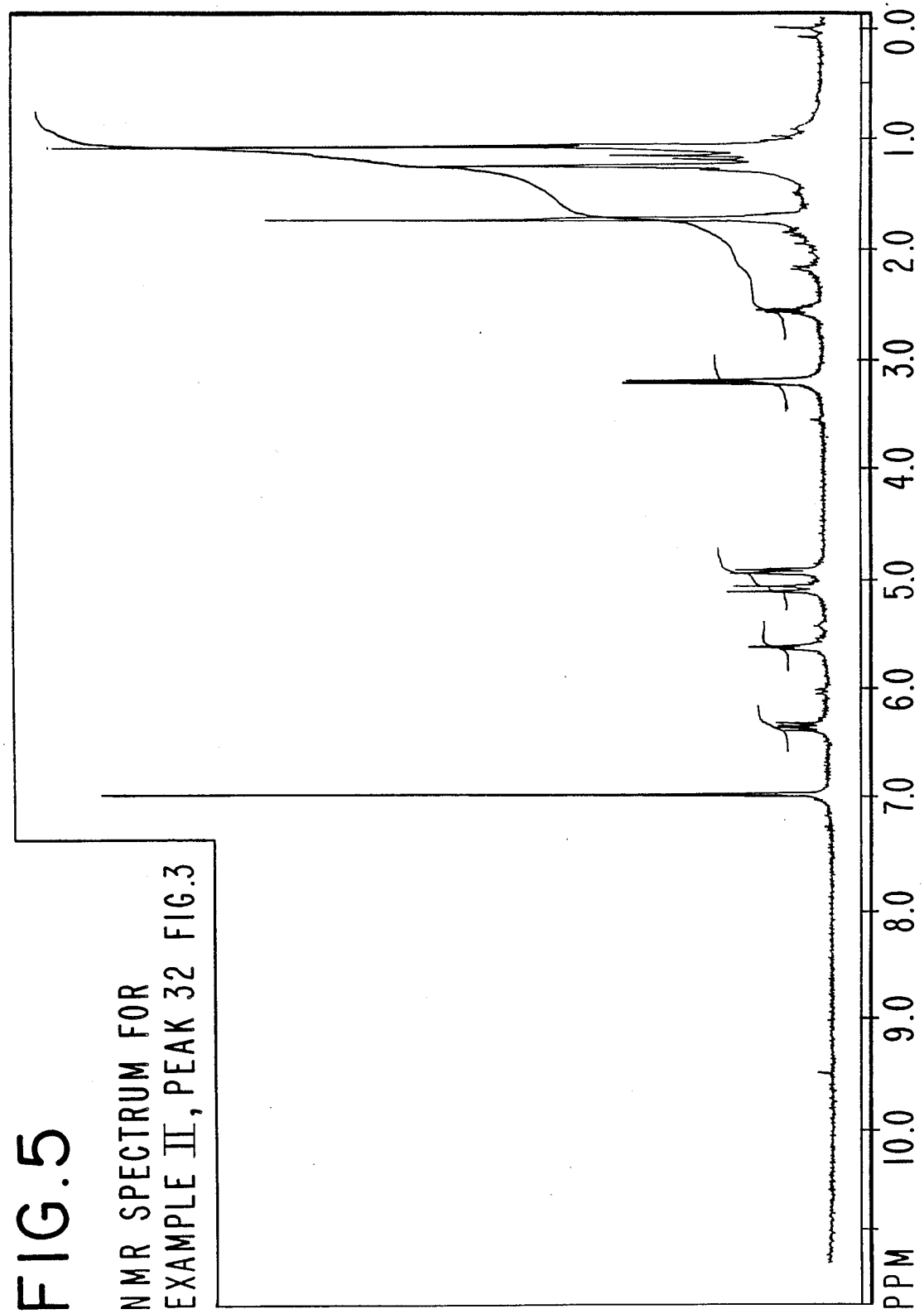
Figure 6:
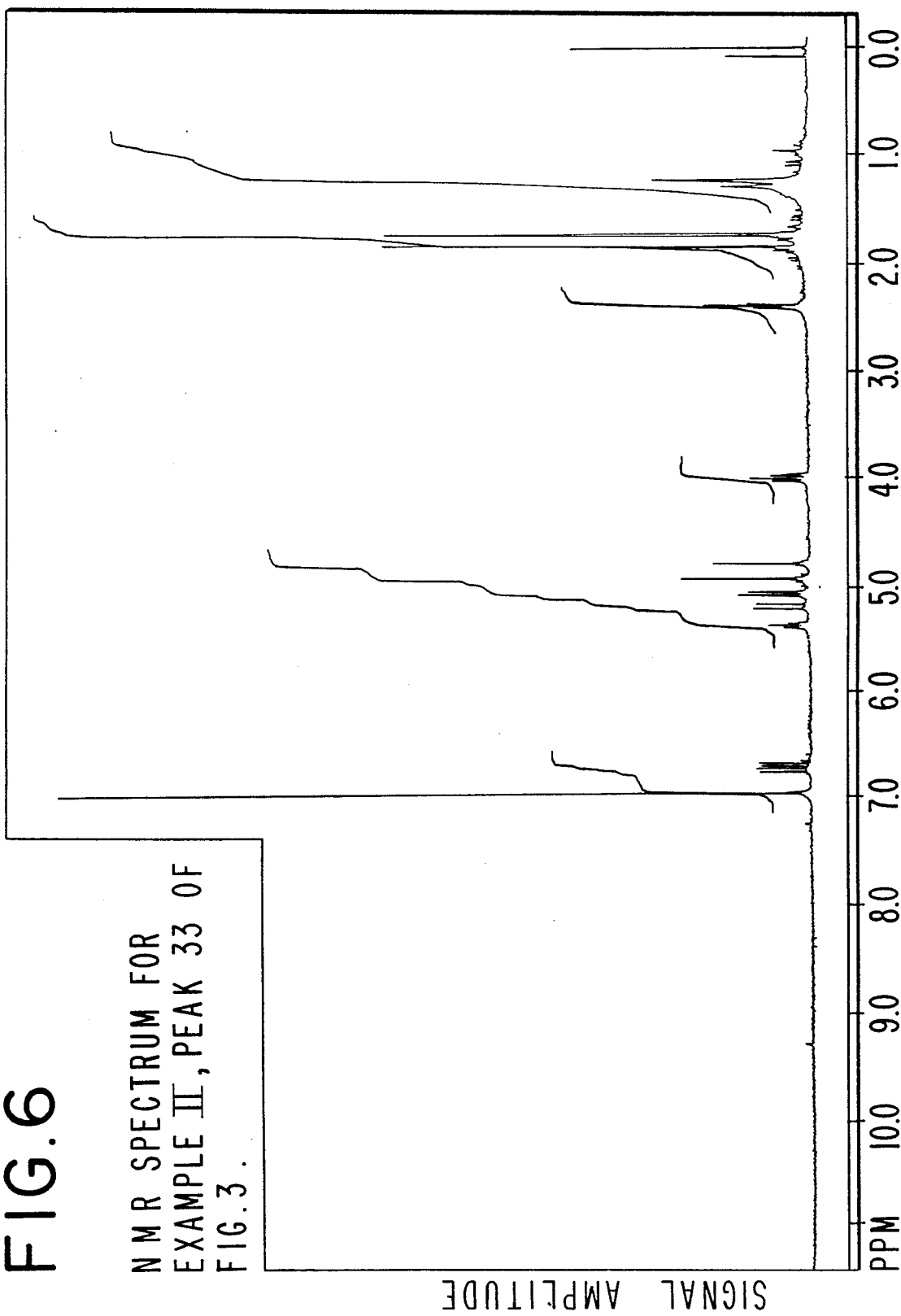

FIG. 5 is the NMR spectrum for the peak indicated by reference numeral 32 of FIG. 3 for the compound having the structure:

FIG. 6 is the NMR spectrum for the peak indicated by reference numeral 33 of the GLC profile of FIG. 3 (Example II) for the compound having the structure:

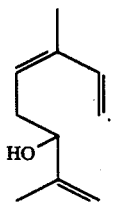

Figure 7:
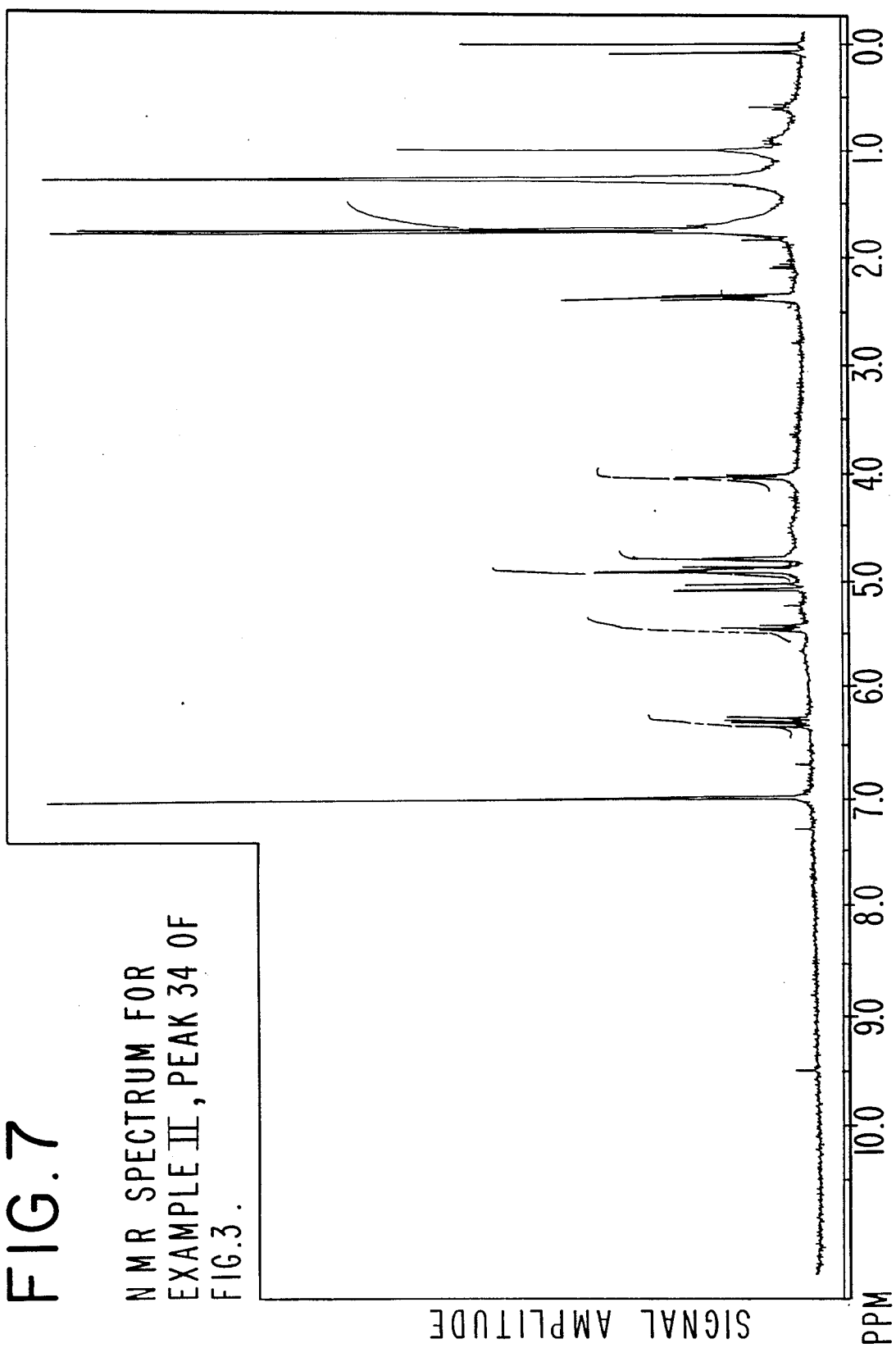

FIG. 7 is the NMR spectrum for the peak indicated by reference numeral 34 of the GLC profile of FIG. 3 (Example II) for the compound having the structure:

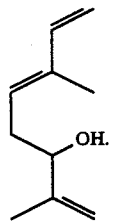

Figure 2:
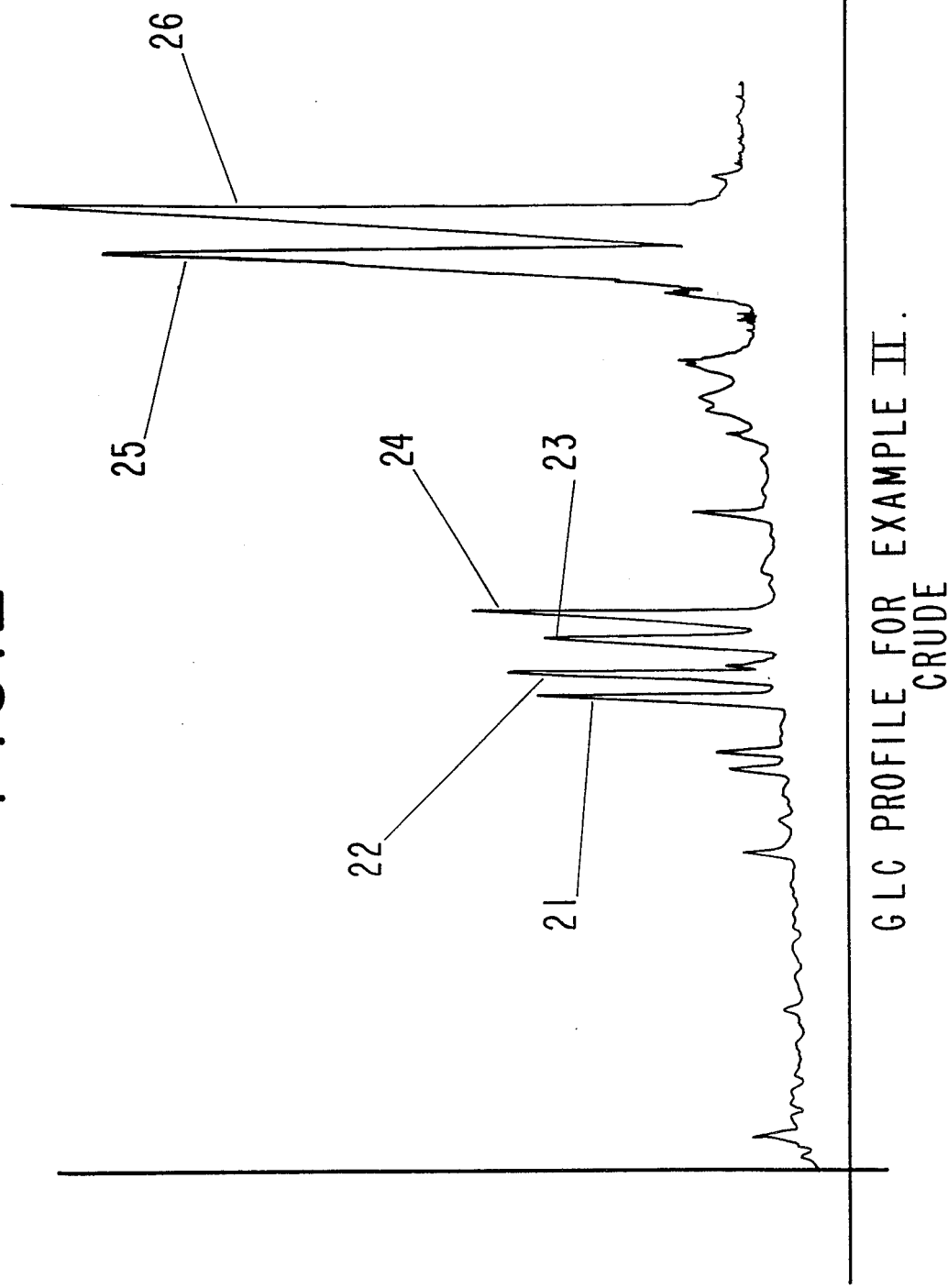
FIG. 2 is the GLC profile of the crude reaction product of Example II prior to distillation (Conditions: OV-1 column programmed at 80°–200° C. at 4° C. per minute).
Figure 8:
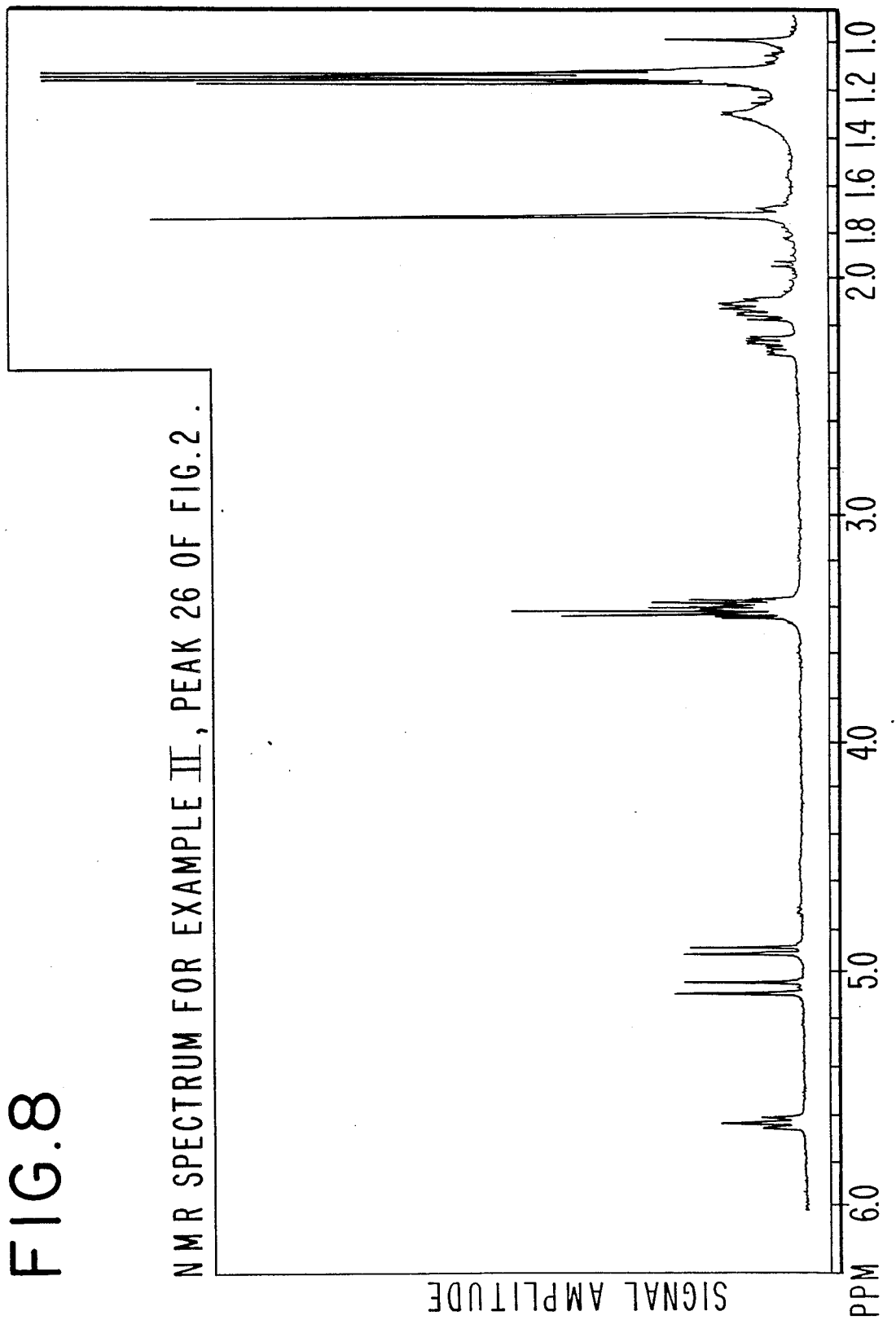

FIG. 8 is the NMR spectrum for the peak indicated by reference numeral 26 of FIG. 2 for the compound having the structure:

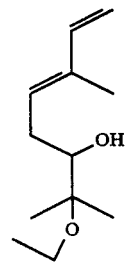

(Example II).

Figure 9:
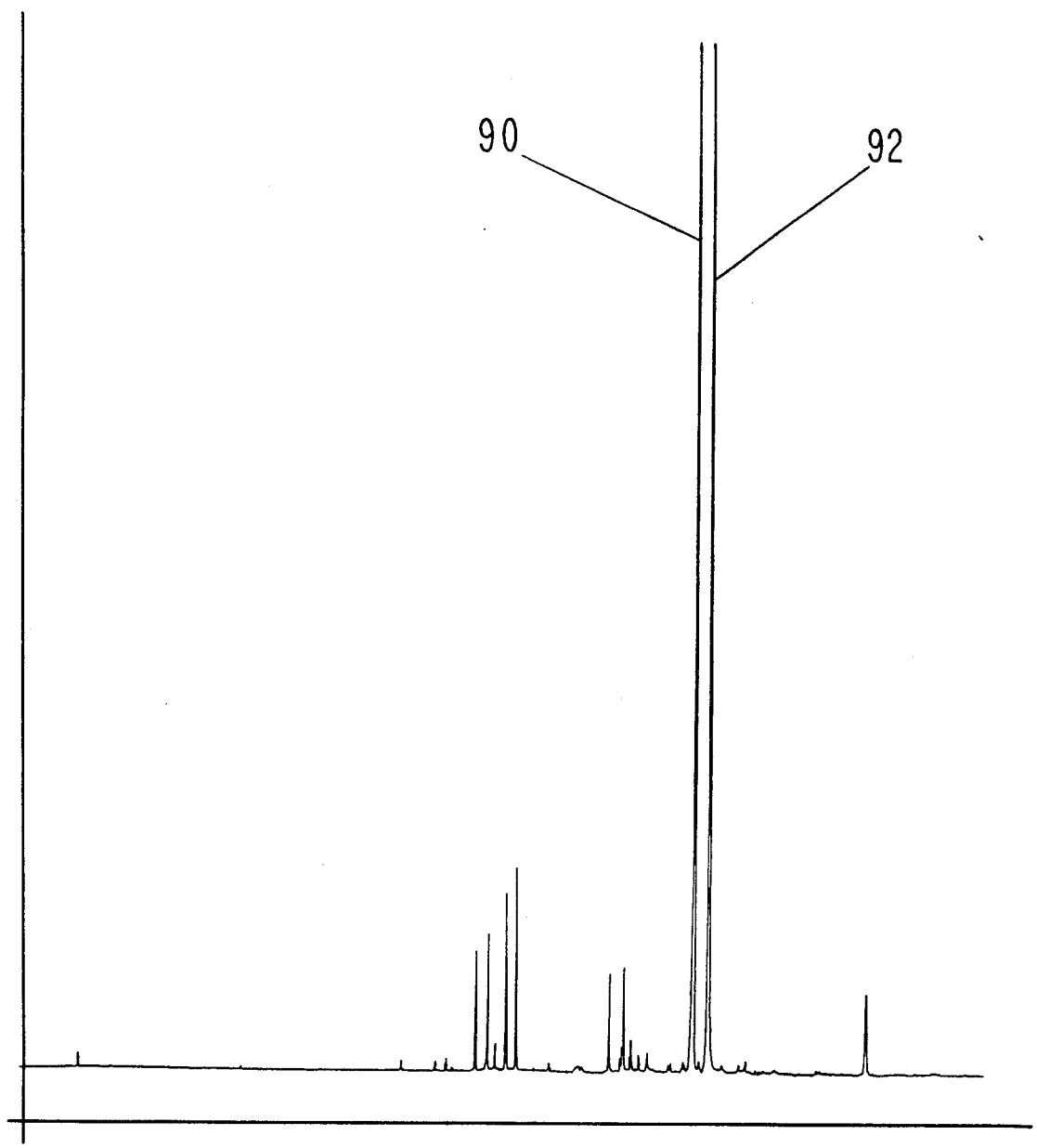

FIG. 9 is the GLC profile for the crude reaction product of Example III (Conditions: Fused silica OV-1 column programmed at 60°–220° C. at 2° C. per minute).

Figure 10:
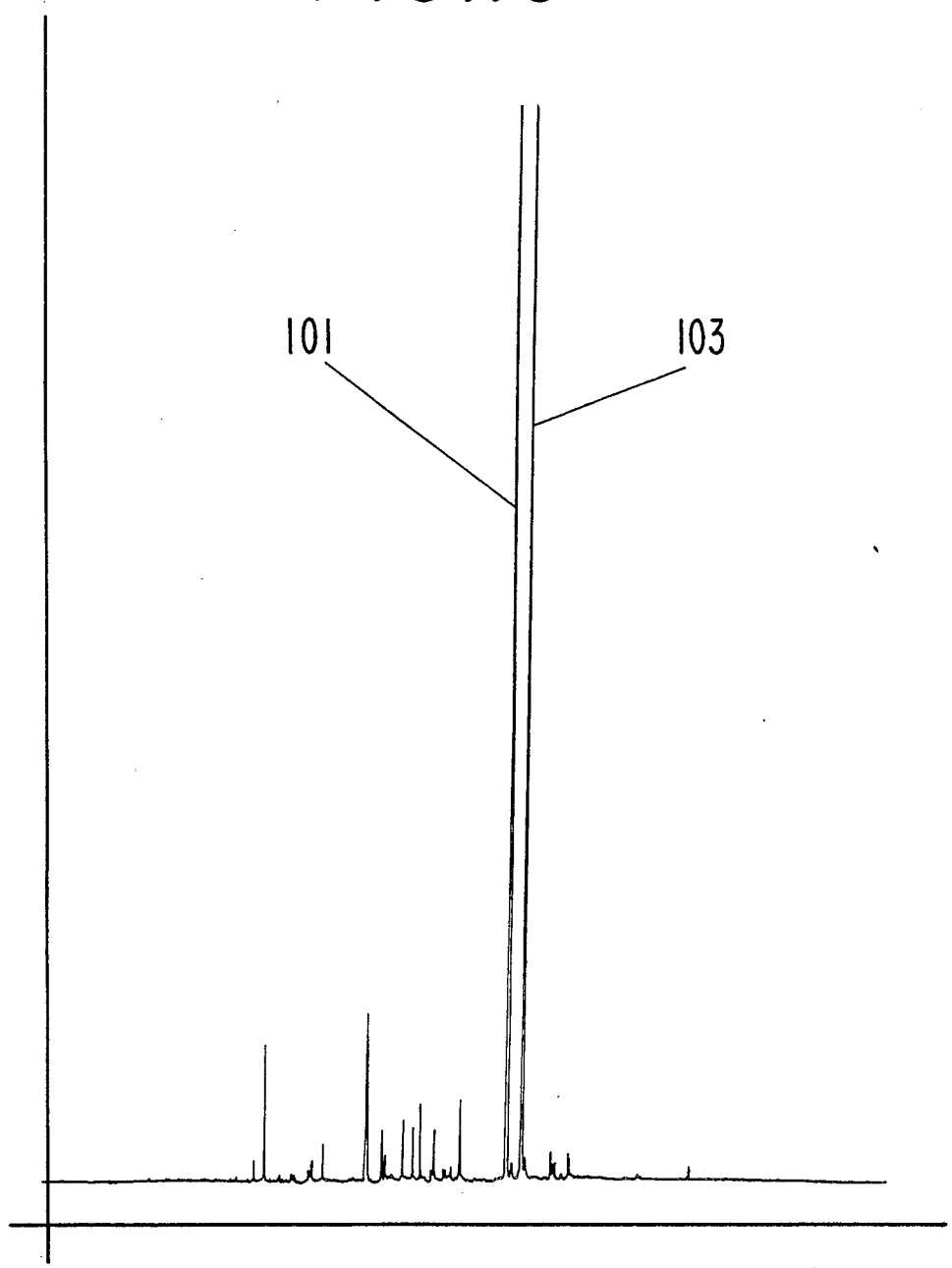

FIG. 10 is the GLC profile for distillation fraction 11 of Example III containing the compounds having the structures:

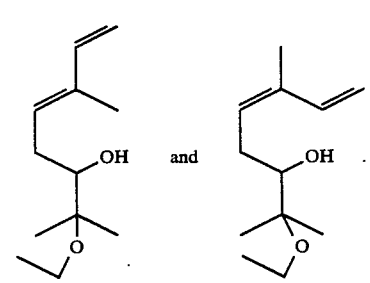

Figure 11:
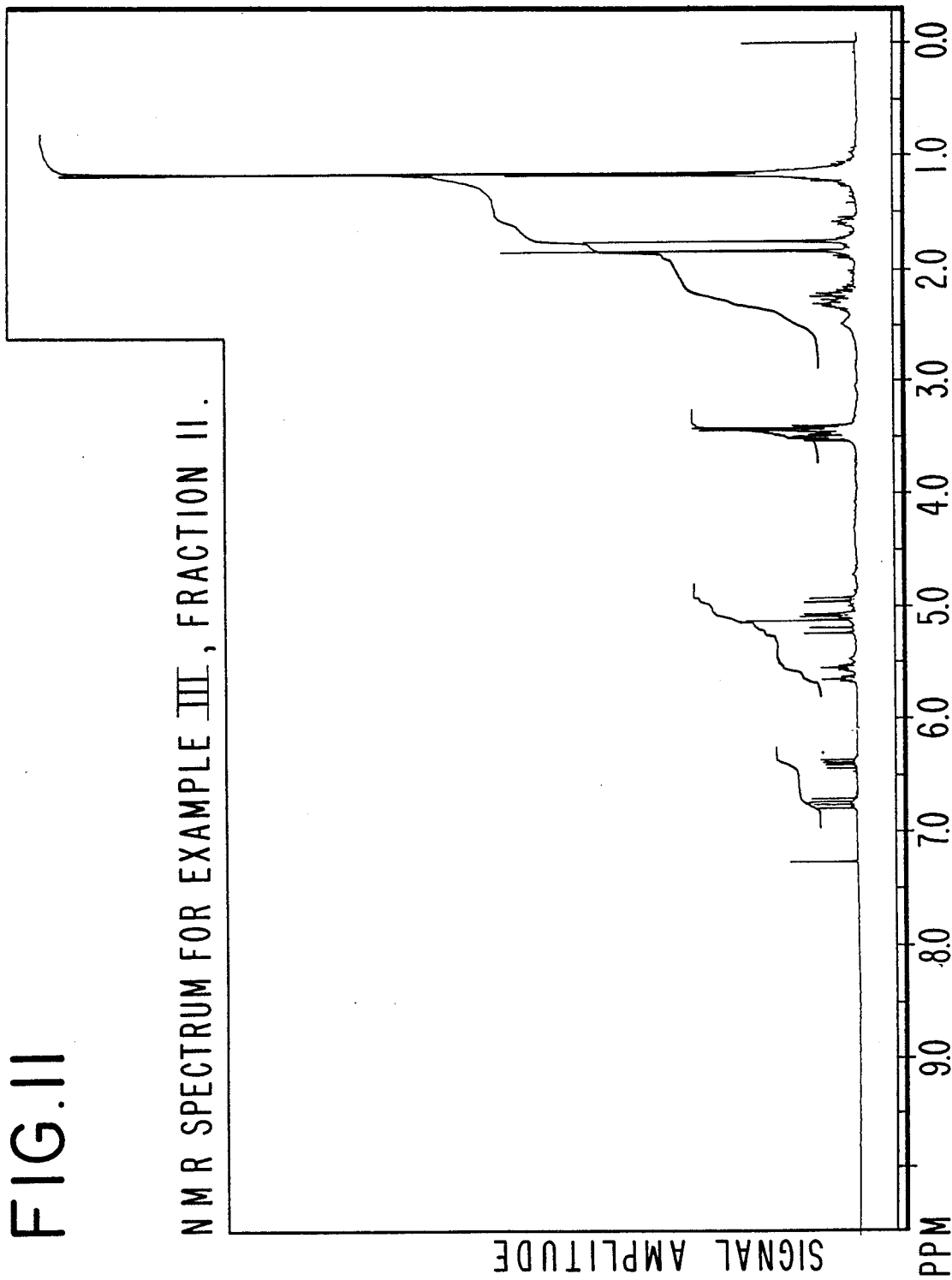

FIG. 11 is the NMR spectrum for distillation fraction 11 of the distillation of the reaction product of Example III containing the compounds having the structures:

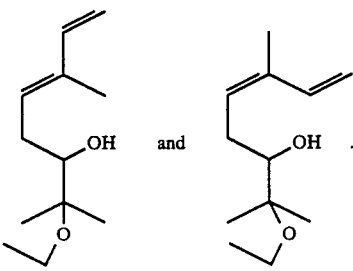

Figure 12:
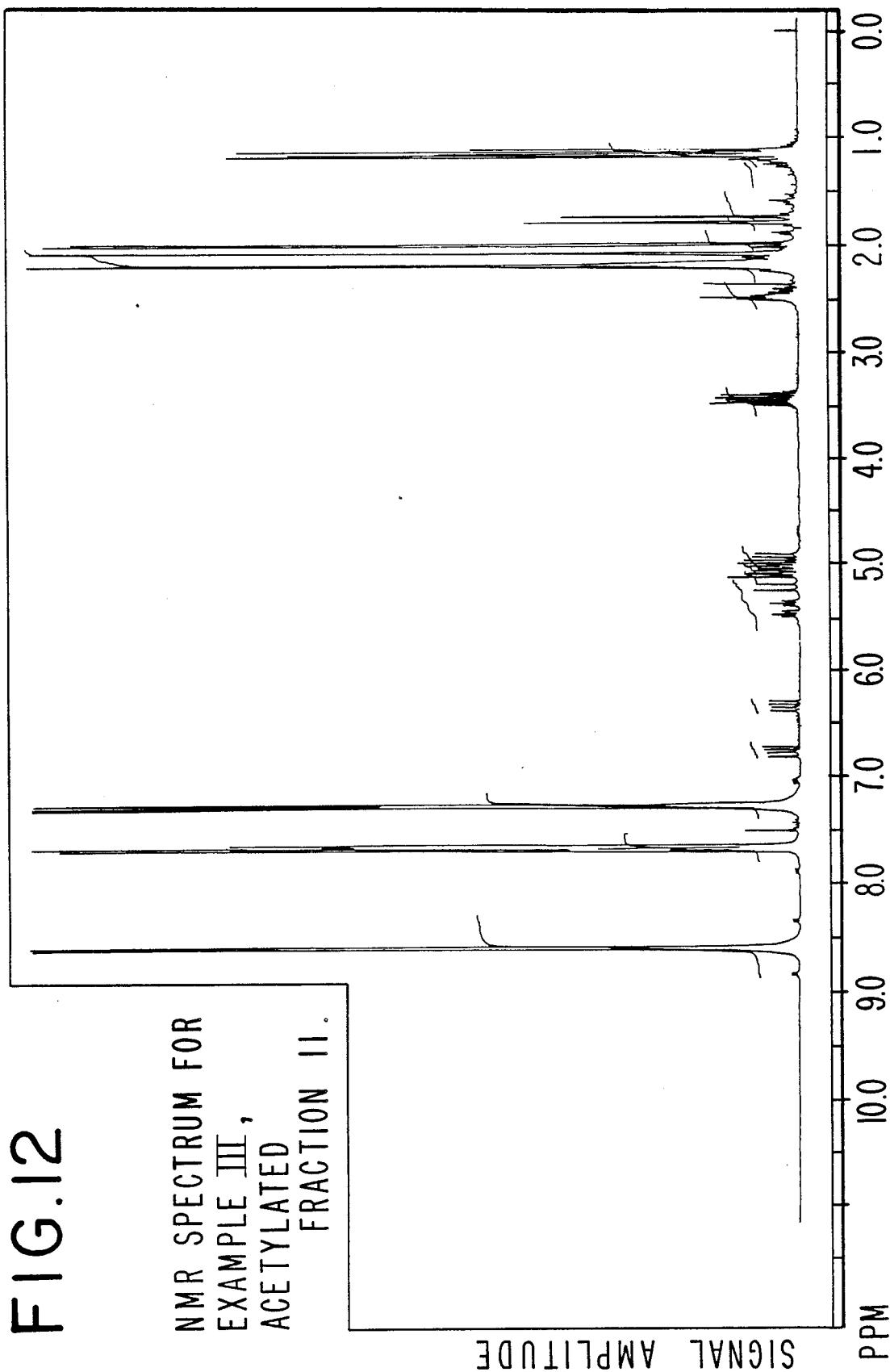

FIG. 12 is the NMR spectrum for the acetylated fraction 11 of the distillation of the reaction product of Example III containing the compounds having the structures:

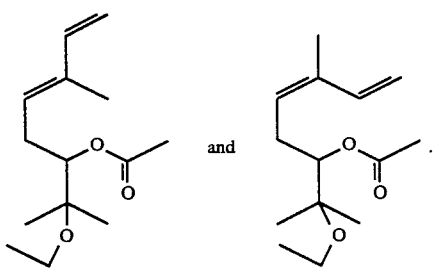

Figure 13:
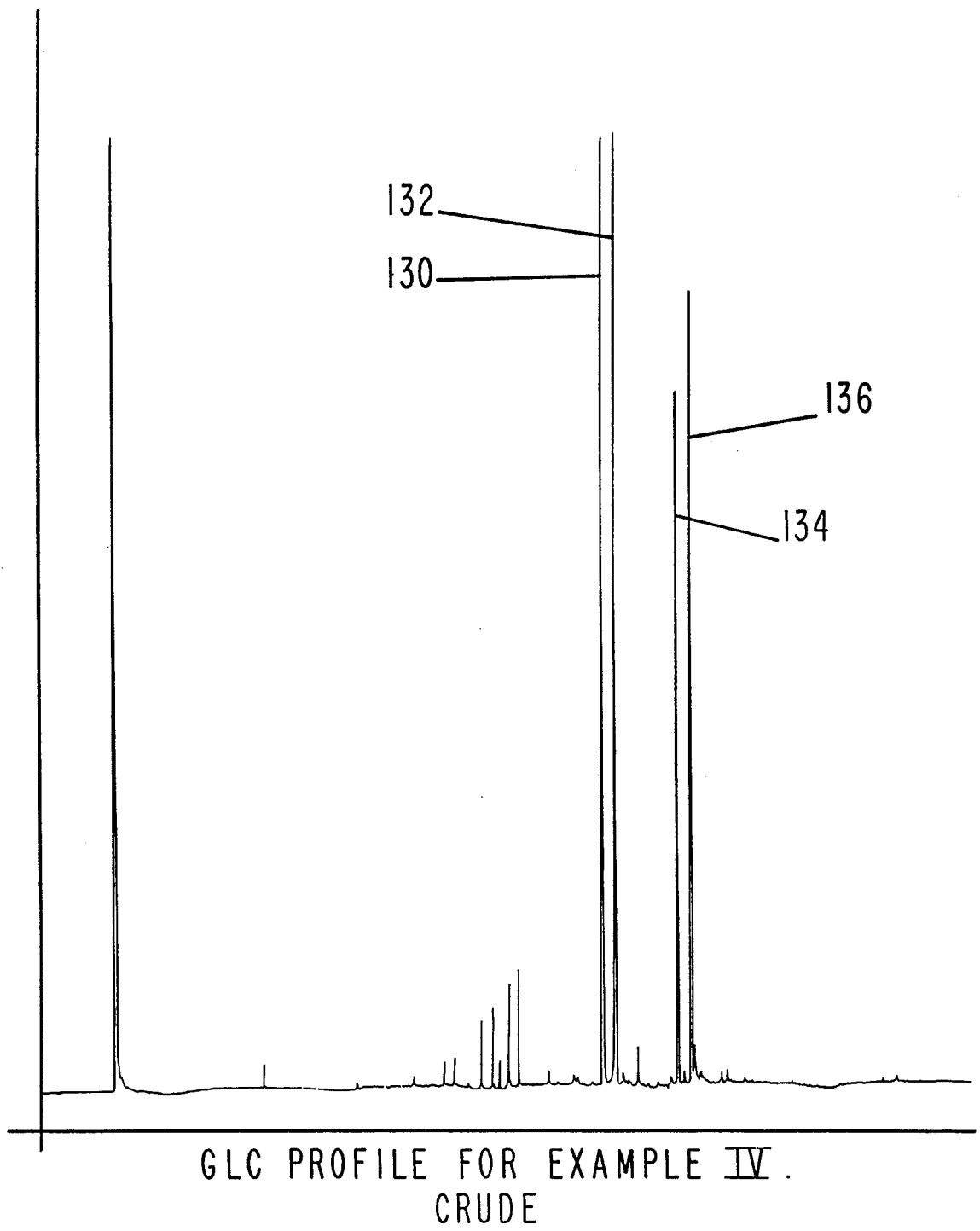

FIG. 13 is the GLC profile for the crude reaction product of Example IV containing the compounds having the structures:

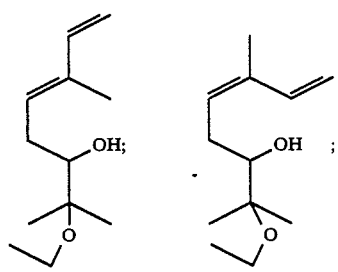

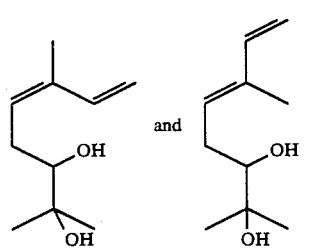

(Conditions: OV-1 column programmed at 60°–220° C. at 4° C. per minute).

Figure 14:
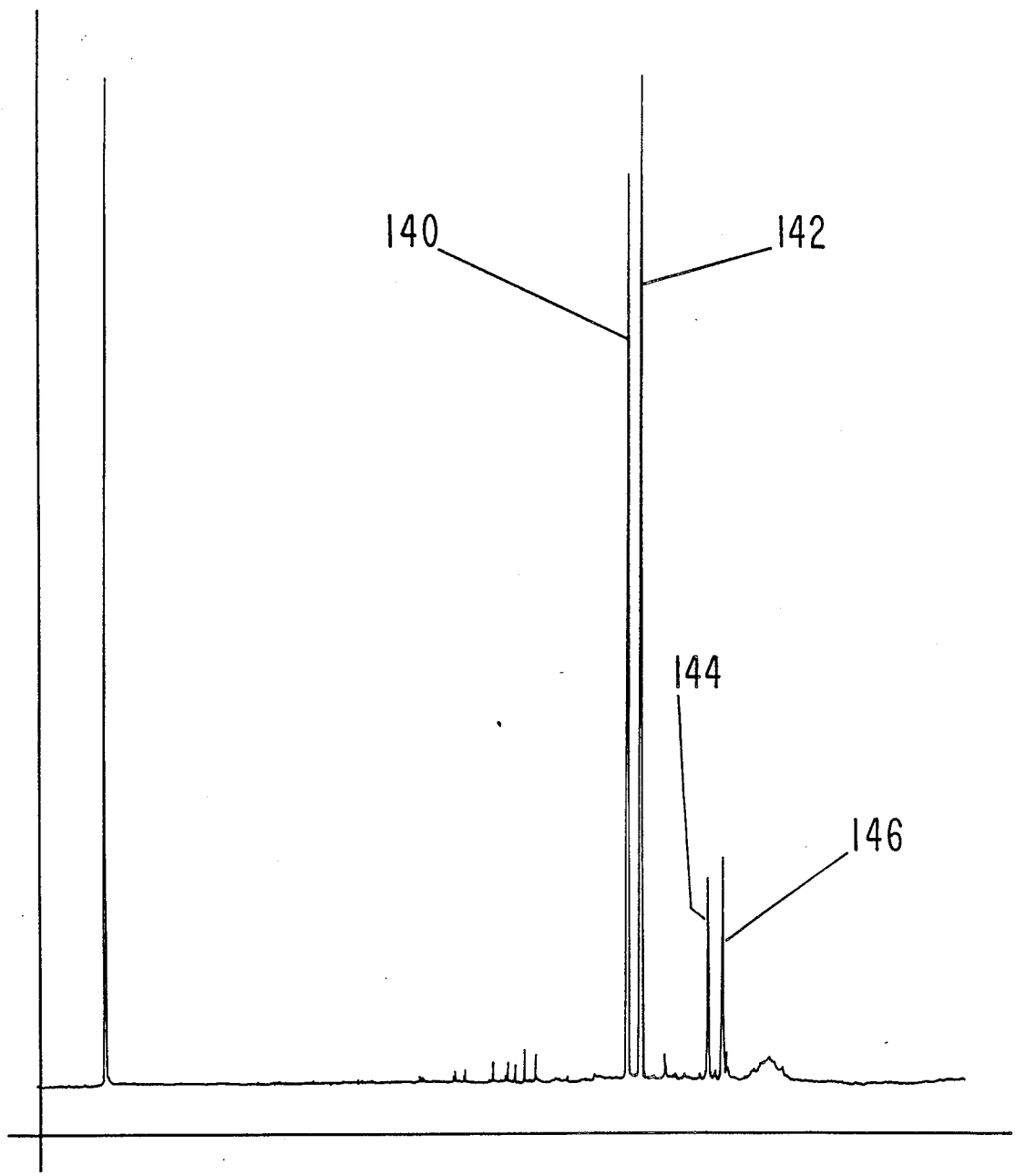

FIG. 14 is the GLC profile for the crude reaction product of Example V(A) containing the compounds having the structures:

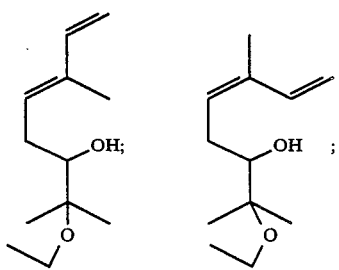

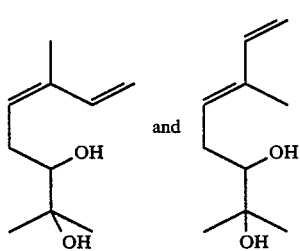

(Conditions: 50M×0.32 mm fused silica OV-1 column programmed at 60°–220° C. at 4° C. per minute).

Figure 15:
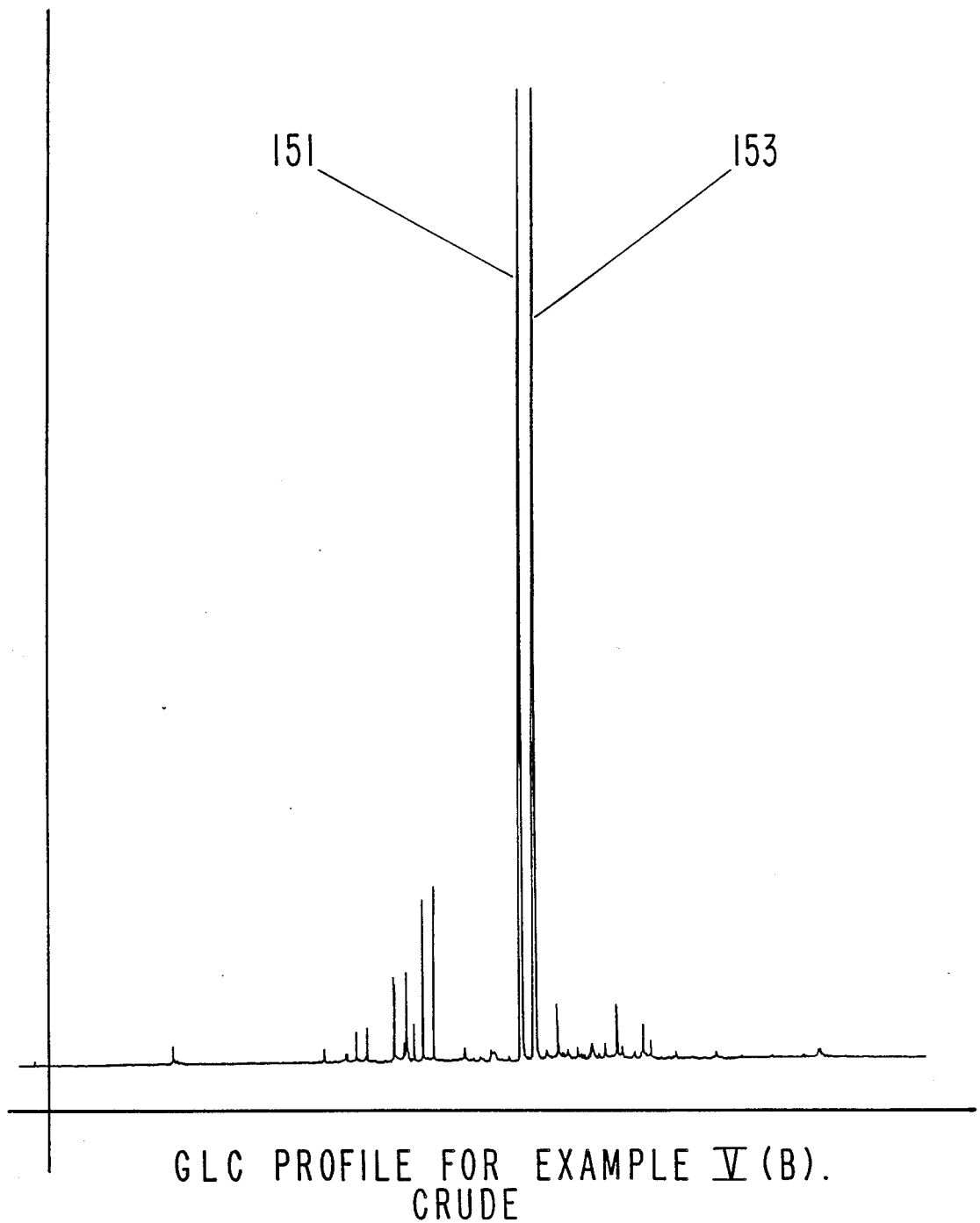

FIG. 15 is the GLC profile for the crude reaction product of Example V(B) containing the compounds having the structures:

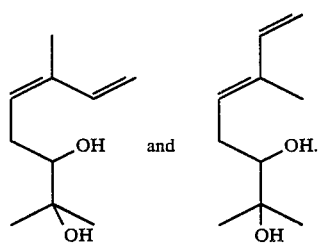

Figure 16:
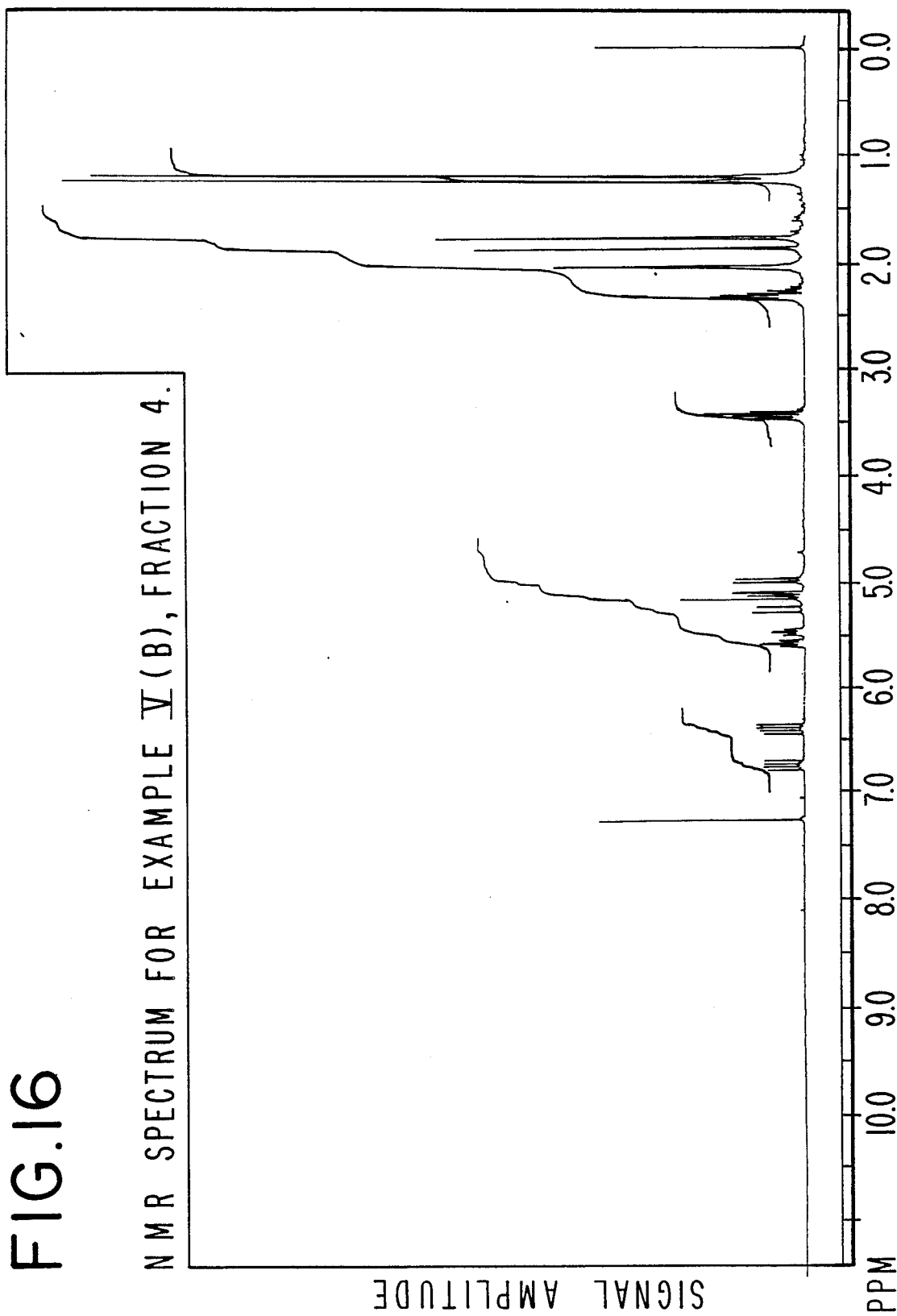

FIG. 16 is the NMR spectrum for distillation fraction 4 of the distillation of the reaction product of Example V(B) containing the compounds having the structures:

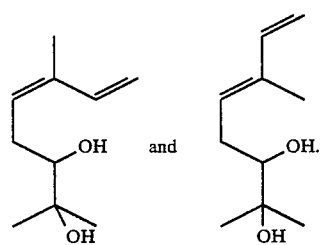

Figure 17:
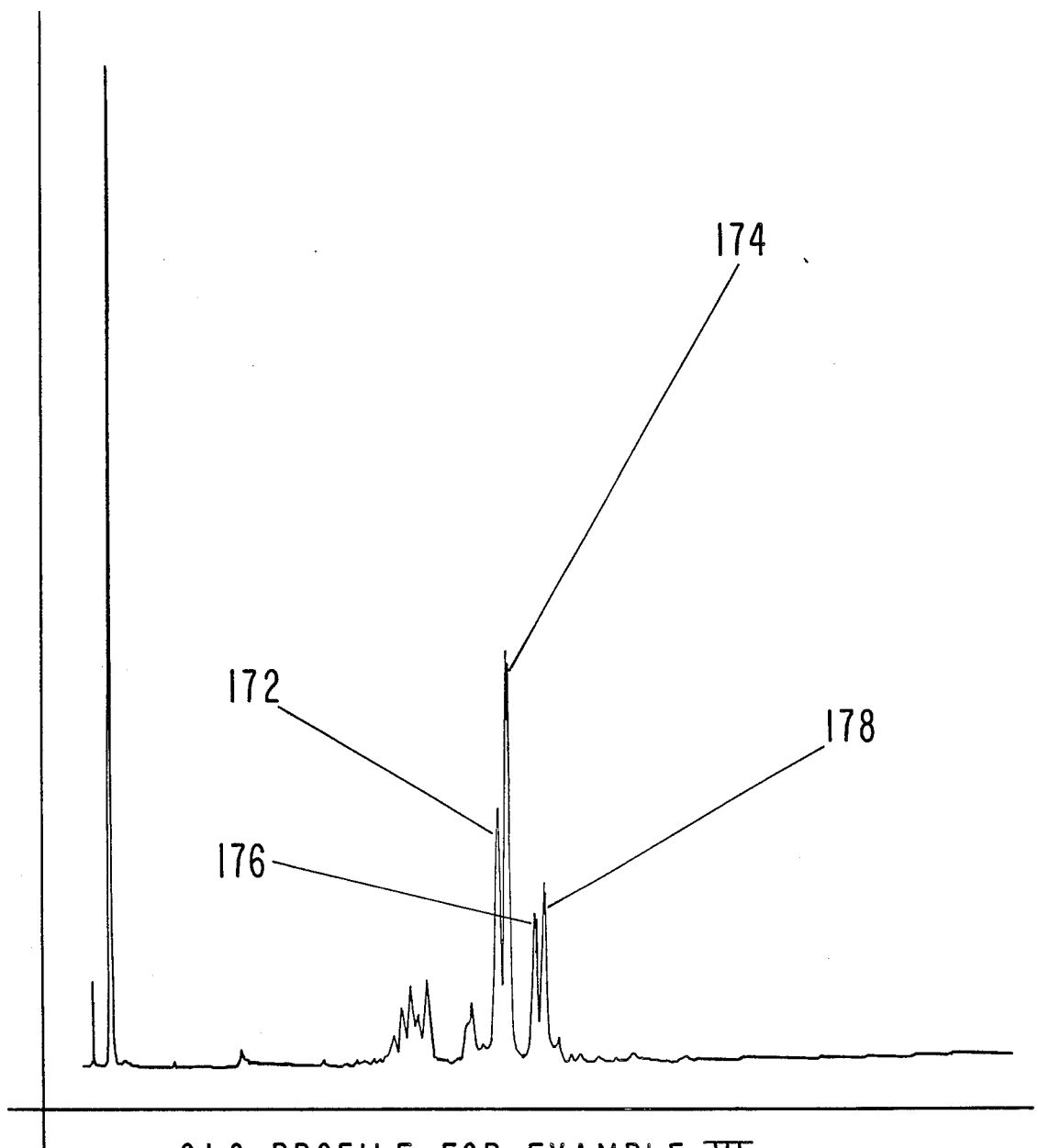

FIG. 17 is the GLC profile for the crude reaction product of Example VI containing the compounds having the structures:

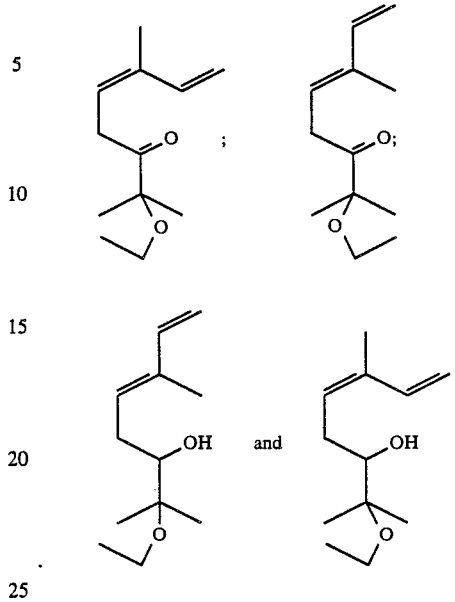

Figure 18:

FIG. 18 is the NMR spectrum for the peaks indicated by reference numerals 172 and 174 of the GLC profile of FIG. 17 containing the compounds having the structures:

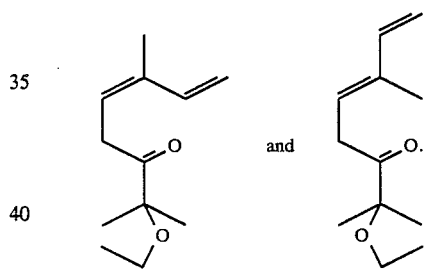

Figure 19:
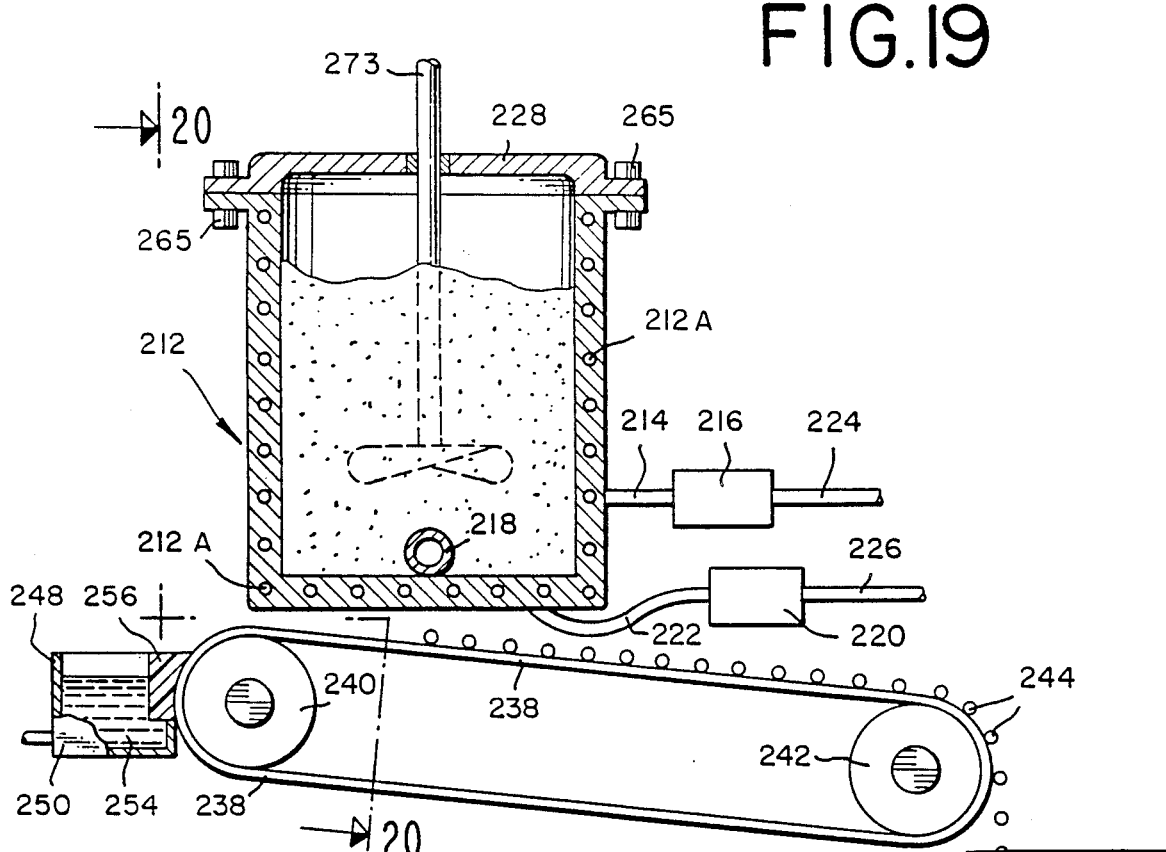

FIG. 19 represents a cut-away side elevation view of the apparatus used in forming perfumed polymers which contain imbedded therein at least one of the 3,7-dimethyl-6,7-dioxo-1,3-octadienes of our invention.

Figure 20:
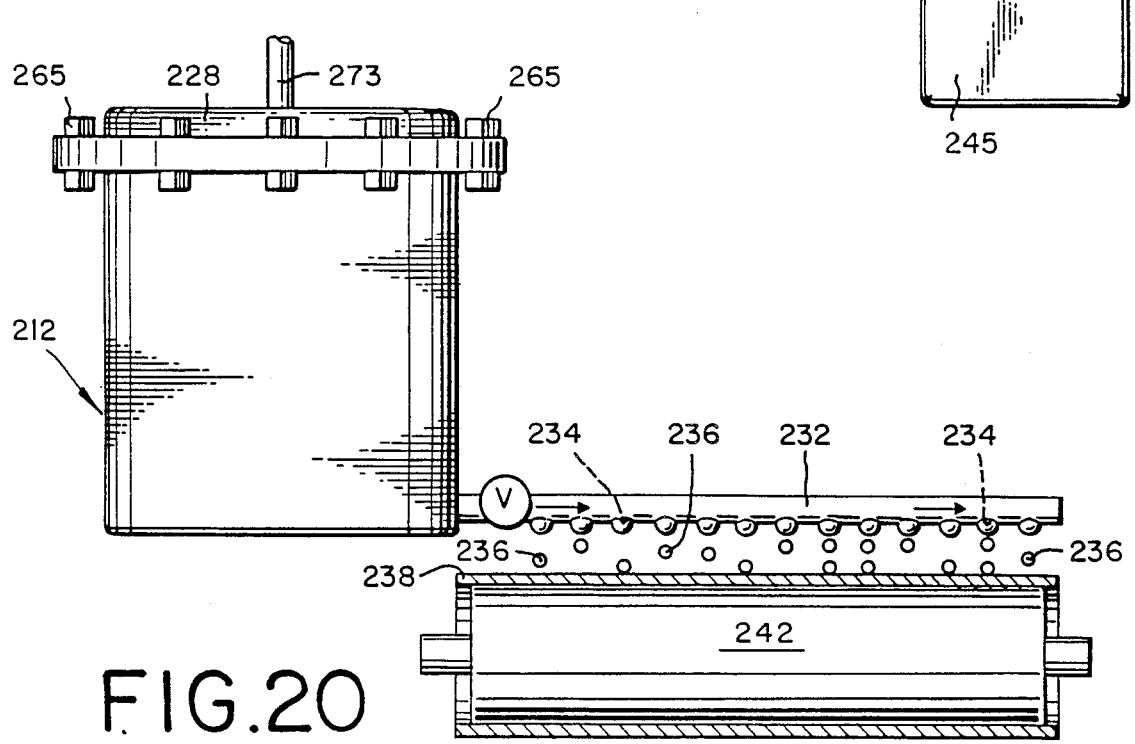

FIG. 20 is a front view of the apparatus of FIG. 19 looking in the direction of the arrows along lines 20—20.

Figure 21:
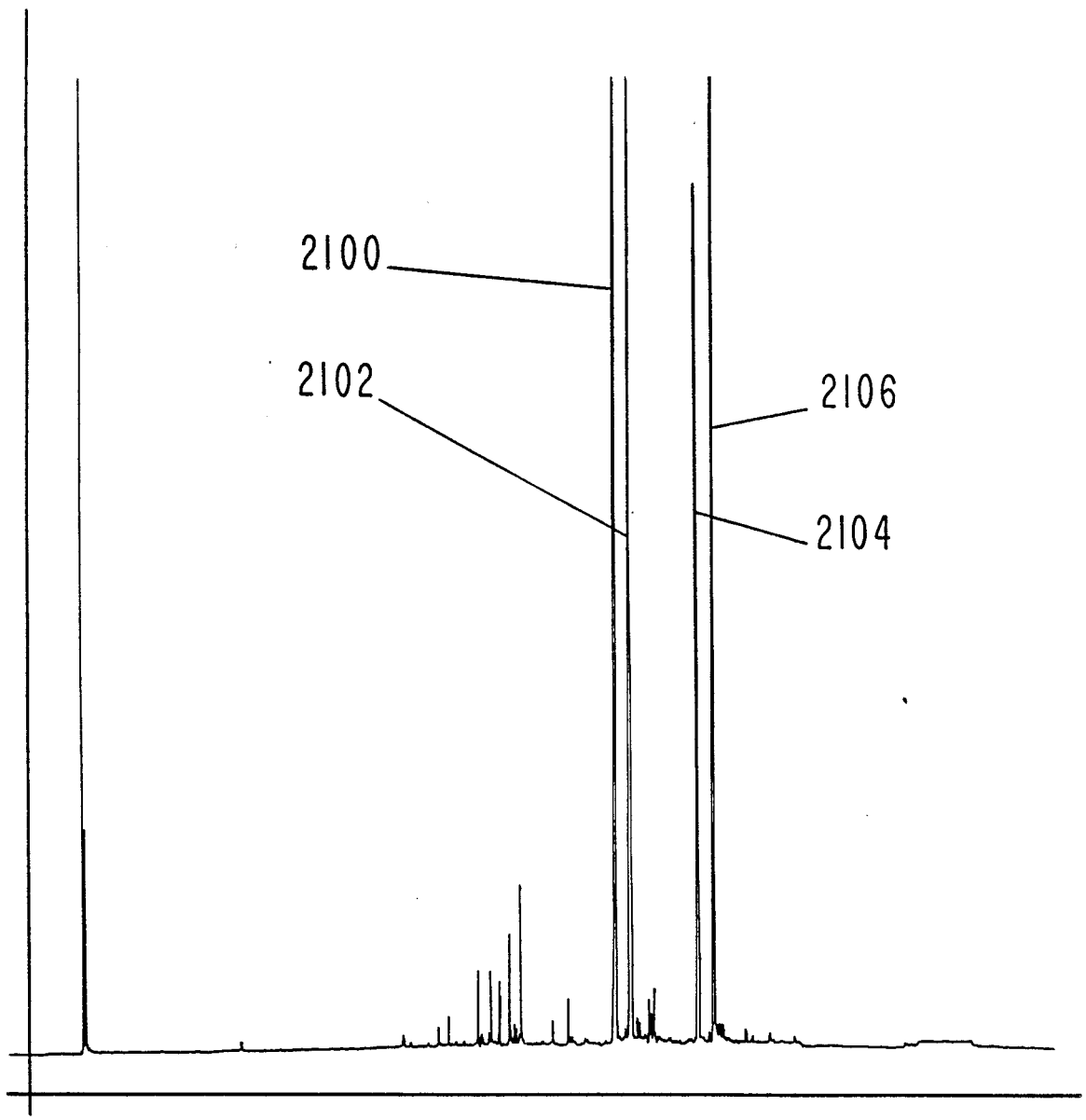

FIG. 21 is the GLC profile for the crude reacton product (prior to distillation) of Example VII containing the compounds having the structures:

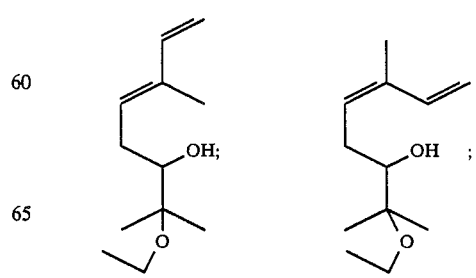

-continued

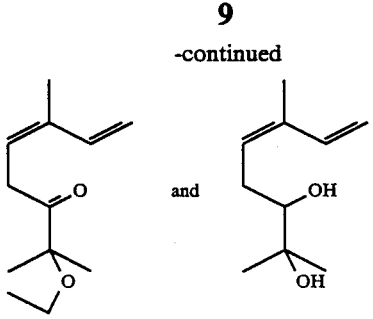

(Conditions: Fused silia OV-1 column programmed at 60°-220° C. at 4° C. per minute).

Figure 22:
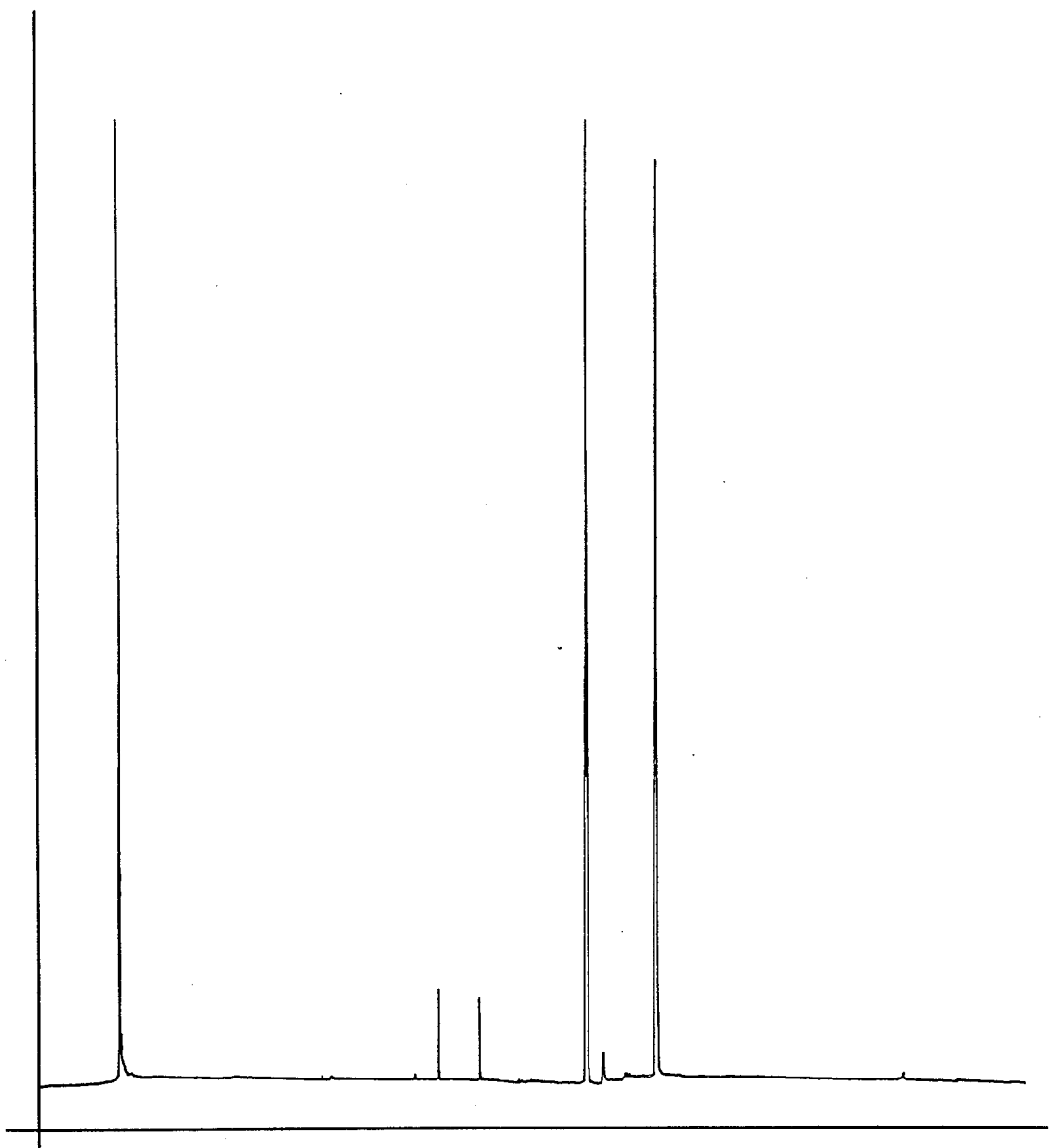

FIG. 22 is the GLC profile for the crude reaction product of Example VIII containing the compounds having the structures:

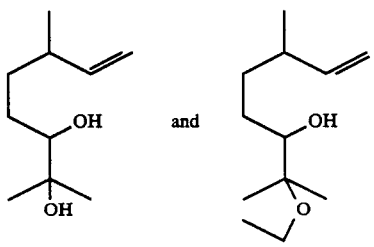

(Conditions: 50M×0.32 mm OV-1 fused silica column programmed at 60°-220° C. at 4° C. per minute).

FIG. 23 is the NMR spectrum for the compound having the structure:

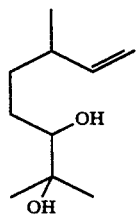

prepared according to Example VIII.

FIG. 24 is the NMR spectrum for the compound having the structure:

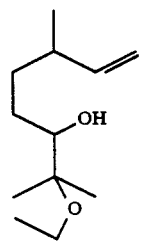

prepared according to Example VIII.

DETAILED DESCRIPTION OF THE DRAWINGS

Figure 1:
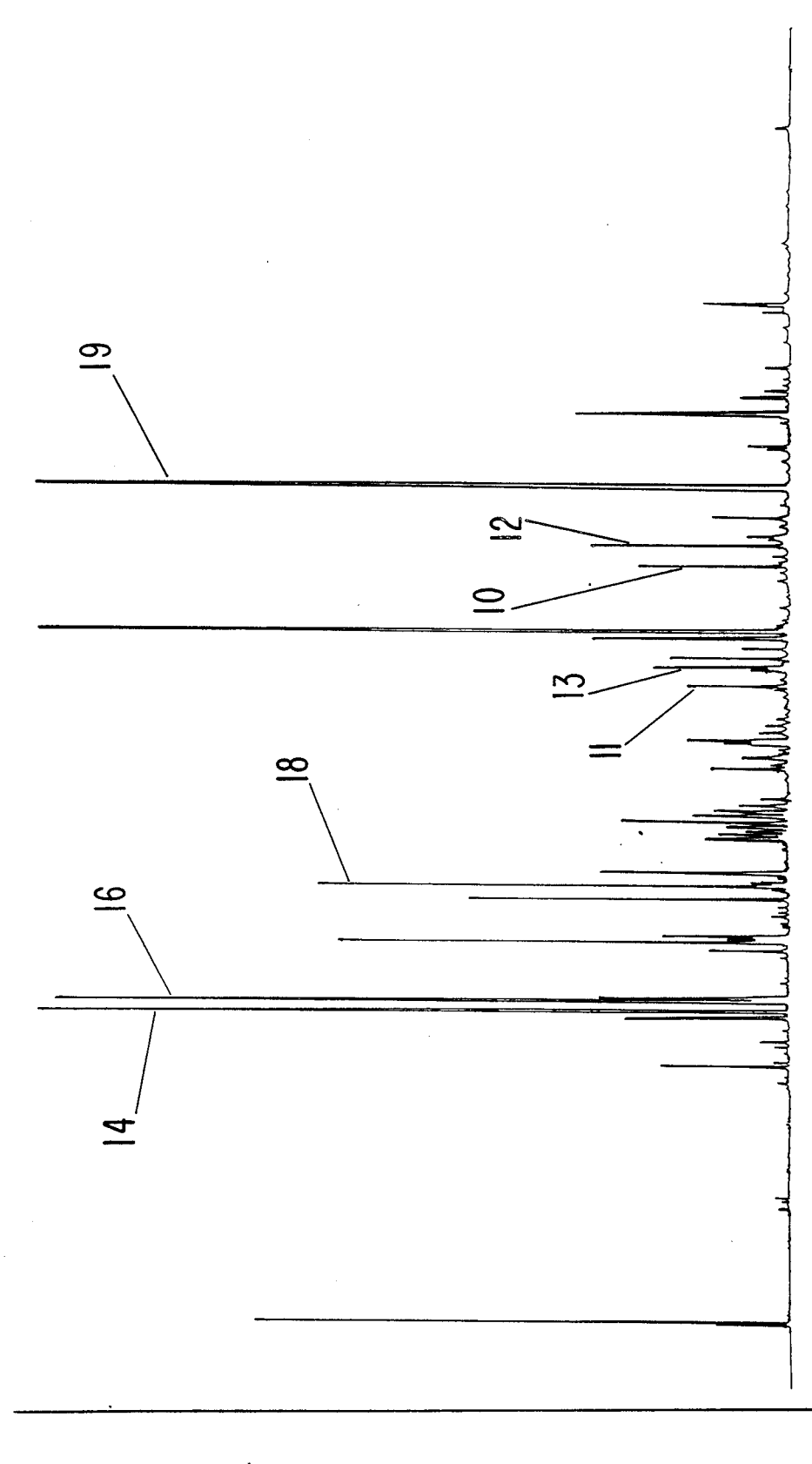
FIG. 1 is a GLC profile of the neutrals of marigold absolute isolated using steam distillation (Conditions: 50M ×0.32 mm OV-1 column programmed at 60°–220° C. at 2° C. per minute).

FIG. 1 is the GLC profile of the neutrals of the steam distillate of marigold absolute (Conditions: 50M×0.32 mm OV-1 column programmed at 60°-220° C. per minute). The peak indicated by reference numeral 14 is the peak for cis-ocimene. The peak indicated by reference numeral 16 is the peak for dihydrotagetone. The peak indicated by reference numeral 18 is the peak for transicimene epoxide. The peaks indicated by reference numerals 11 and 13 are the peaks for the compounds having the structures:

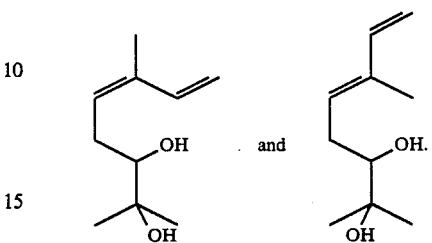

The peaks indicated by reference numerals 10 and 12 are the peaks for the compounds having the structures:

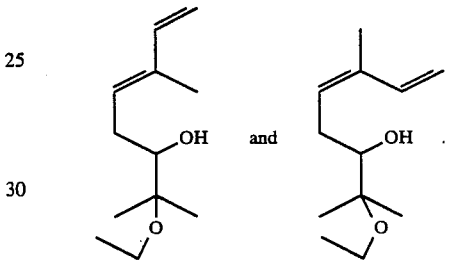

The peak indicated by reference numeral 19 is the peak for caryophyllene. Other peaks on this GLC profile include beta-phallandrene, myrcene, alpha-elemene, alpha-pharnacene, ethyl tetradecanoate and benzyl benzoate, interalia.

FIG. 2 is the GLC profile for the crude reaction product of Example II (Conditions: OV-1 column programmed at 80°-200° C. at 4° C. per minute). The peak indicated by reference numeral 21 is the peak for the compound having the structure:

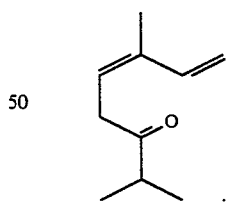

The peak indicated by reference numeral 22 is the peak for the compound having the structure:

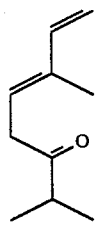

The peak indicated by reference numeral 23 is the peak for the compound having the structure:

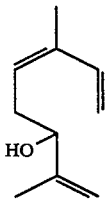

The peak indicated by reference numeral 24 is the peak for the compound having the structure:

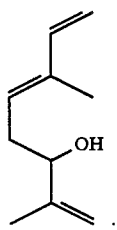

The peak indicated by reference numeral 25 is the peak for the compound having the structure:

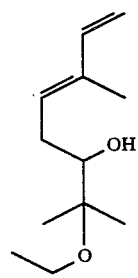

The peak indicated by reference numeral 26 is the peak for the compound having the structure:

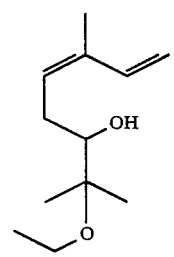

FIG. 3 is the GLC profile for distillation fraction 2 of the distillation of the reaction product of Example II (Conditions: OV-1 column programmed at 80°–220° C. at 4° C. per minute). The peak indicated by reference numeral 31 is the peak for the compound having the structure:

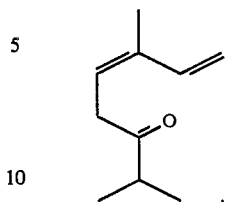

The peak indicated by reference numeral 32 is the peak for the compound having the structure:

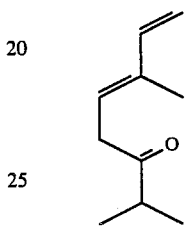

The peak indicated by reference numeral 33 is the peak for the compound having the structure:

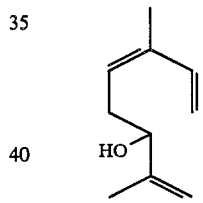

The peak indicated by reference numeral 34 is the peak for the compound having the structure:

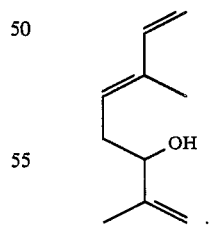

FIG. 9 is the GLC profile for the crude reaction product of Example III (Conditions: Fused silica OV-1 column programmed at 60°–220° C. at 2° C. per minute). The peaks indicated by reference numerals 90 and 92 are the peaks for the compounds having the structures:

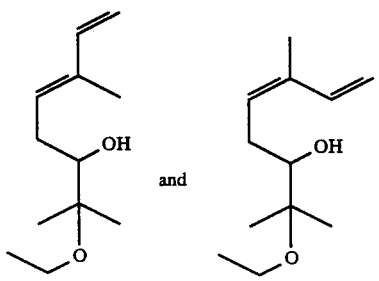

(ratio: 34.2:39.2).

FIG. 10 is the GLC profile for distillation fraction 11 of the distillation of the reacton product of Example III (Conditions: OV-1 column programmed at 60°-220° C. at 2° C. per minute). The peaks indicated by reference numerals 101 and 103 are the peaks for the compounds having the structures:

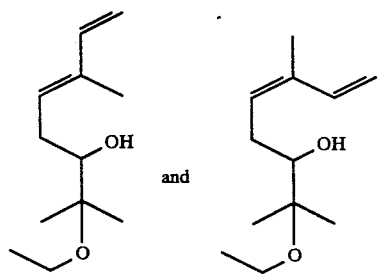

(ratio: 43.5:38).

FIG. 13 is the GLC profile for the crude reaction product of Example IV (Conditions: OV-1 column programmed at 60°-220° C. at 4° C. per minute). The peaks indicated by reference numerals 130 and 132 are the peaks for the compounds having the structures:

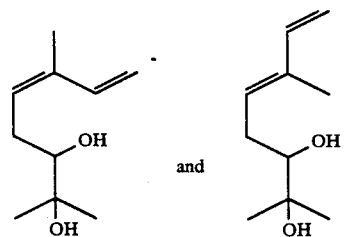

(ratio: 24:27). The peaks indicated by reference numerals 134 and 136 are the peaks for the compounds having the structures:

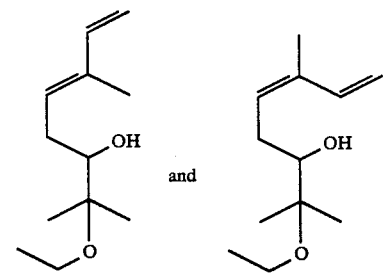

(ratio: 16:29).

FIG. 14 is the GLC profile for the crude reaction product of Example V(A) (Conditions: 50M×0.32 mm fused silica OV-1 column programmed at 60°-220° C. at 4° C. per minute). The peaks indicated by reference numerals 140 and 142 are for the compounds having the structures:

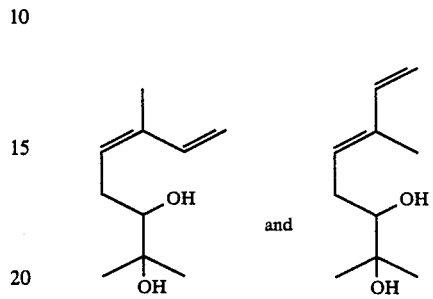

(35.0% and 40% of reaction product). The peaks indicated by reference numerals 144 and 146 are the peaks for the compounds having the structures:

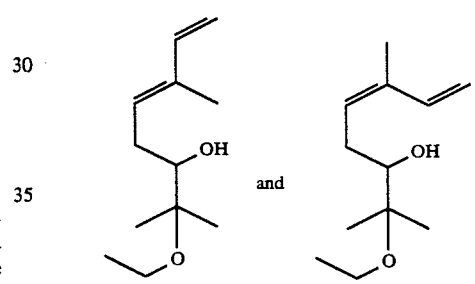

(7.3 and 7.8% of the reaction product).

FIG. 15 is the GLC profile for the crude reaction product of Example V(B) (Conditions: 50M×0.32 mm fused silica OV-1 column programmed at 60°-220° C. at 4° C. per minute). The peaks indicated by reference numerals 151 and 153 are for the compounds having the structures:

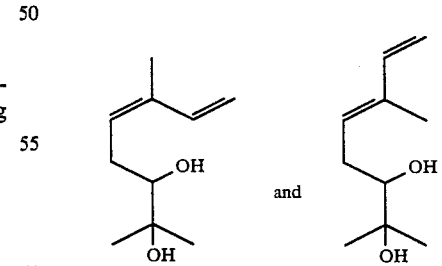

(ratio: 38:44).

FIG. 17 is the GLC profile for the crude reaction product of Example VI (Conditions: SE-30 column programmed at 80°-220° C. at 8° C. per minute). The peaks indicated by reference numerals 172 and 174 are for the compounds having the structures:

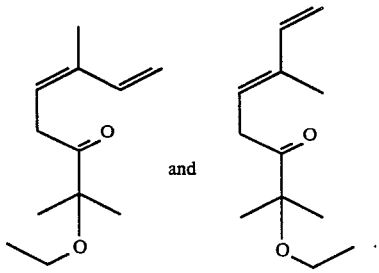

The peaks indicated by reference numerals 176 and 178 are for the compounds having the structures:

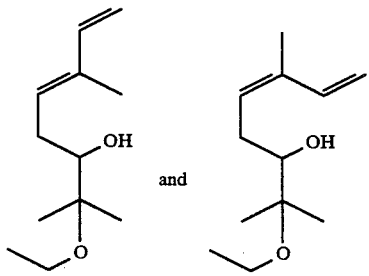

FIG. 21 is the GLC profile for the crude reaction product of Example VII (Conditions: Fused silica OV-1 column programmed at 60°–220° C. at 4° C. per minute). The peaks indicated by reference numerals 2100 and 2102 are for the compounds having the structures:

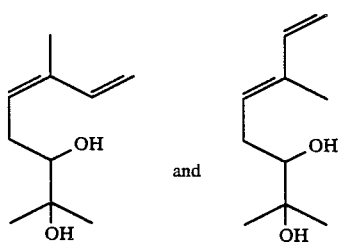

(ratio: 19:29). The peaks indicated by reference numerals 2104 and 2106 are for the compounds having the structures:

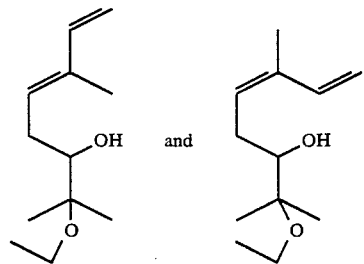

(ratio of percentages: 14%:21%).

Referring to FIGS. 19 and 20, there is provided a process for forming scented polymer elements (wherein the polymer may be a thermoplastic polymer such as a low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles whicy may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, refering to FIGS. 19 and 20, in particular, the apparatus used in producing such elements comprises a device for forming the polymer containing perfume, e.g., polyethylene or polyethylenepolyvinyl acetate or mixtures of same or polypropylene containing at least one of the 3,7-dimethyl-6,7-dioxo-1,3-octadienes of our invention taken alone or taken together with one or more additional perfume materials which comprises a vat or container 212 into which the polymer taken alone or in admixture with other copolymers and the perfuming substance which is at least one of the 3,7-dimethyl-6,7-dioxo-1,3-octadienes of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder having heating coils 212A which are supplied with electric current through cable 214 from a rheostat or control 216 is operated to maintain the temperature inside th container 212 such that the polymer in the container 212 will be maintained in the molten or liquid state. It has been found advantageous to employ polymers at such a temperature that the viscosity will be in the range of 90–100 Saybolt seconds. The heater 218 is maintained to maintain the upper portion of the container 212 within a temperature range of, for example, 220° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which containes at least one of the 3,7-dimethyl-6,7-dioxo-1,3-octadienes of our invention and, if desired, one or more other perfume materials is quickly added to the melt. Generally, about 10–45 percent by weight of the resulting mixture of the perfumery substane is added to the polymer.

After the perfume material is added to the container 212, the mixture is stirred for a few minutes, for example, 5–15 minutes and maintained within the temperature ranges indicated previously by the heating coil 212A and the heater 218. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer is in intimate admixture with at least one of the 3,7-dimethyl-6,7-dioxo-1,3-octadienes of our invention taken alone or taken further together with one or more other perfume substances and in such admixture will continuously drop through the orifices 234 downwardly from the conduit 232. During this time, the temperature of the polymer intimately admixed with the perfumery substance in the container 212 is accuratly controlled so that a temperature in the range of from about 240°–250° C., for example, (in the case of low density polyethylene) will exist in the conduit 232. The regulation of the temperature through the controls 216 and 220 is essential in order to insure temperature balance to provide for the continous drippin or dropping or molten polymer intimately admixed with the perfume substance which is all of or which contains at least one of the 3,7-dimethyl-6,7-dioxo-1,3-octadienes of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instanctaneously and fall off the end of the conveyor 238 into a container 250 which is advantageously filled with water or some other suitable cooling liquid in order to insure the rapid cooling of each of the pellets 244. The pellets 244 are then collected from the container 250 and utilized for the formation of other functional products, e.g., garbage bags and the like.

THE INVENTION

The present invention provides 3,7-dimethyl-6,7-dioxo-1,3-octadienes defined according to the generic structure:

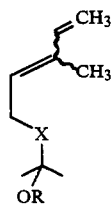

wherein X represents a moiety selected from the group consisting of:

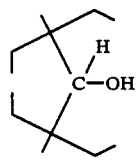

and

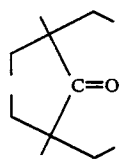

wherein R represents ethyl or hydrogen and wherein the wavy lines represent the "E" or "Z" configuration of the vinyl and methyl moieties about the 3,4-pi-bond of the molecule. The subgenus of the genus having the structure:

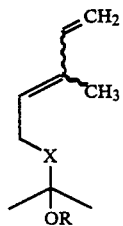

which subgenus has the structure:

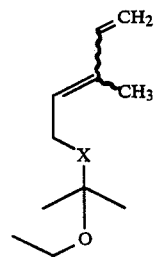

(wherein X and the wavy lines are defined, supra) represents novel compounds.

The present invention also provides a process for preparing the 3,7-dimethyl-6,7-dioxo-1,3-octadienes of our invention defined according to the structure:

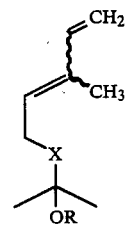

by means of reacting the mixture of myrcene epoxide isomers defined according to the structure:

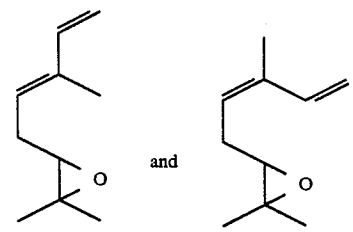

in the presence of an acid catalyst and ethyl alcohol, or in the absence of ethyl alcohol according to one of the reactions:

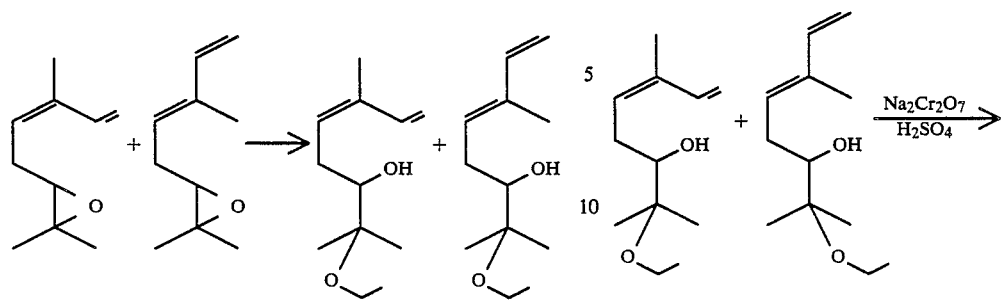
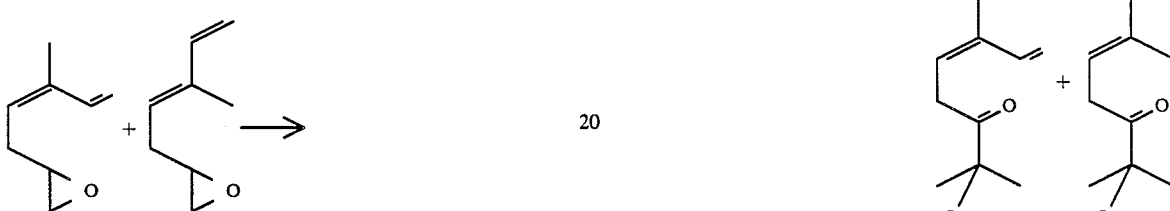
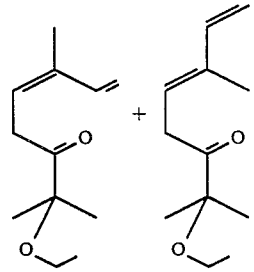
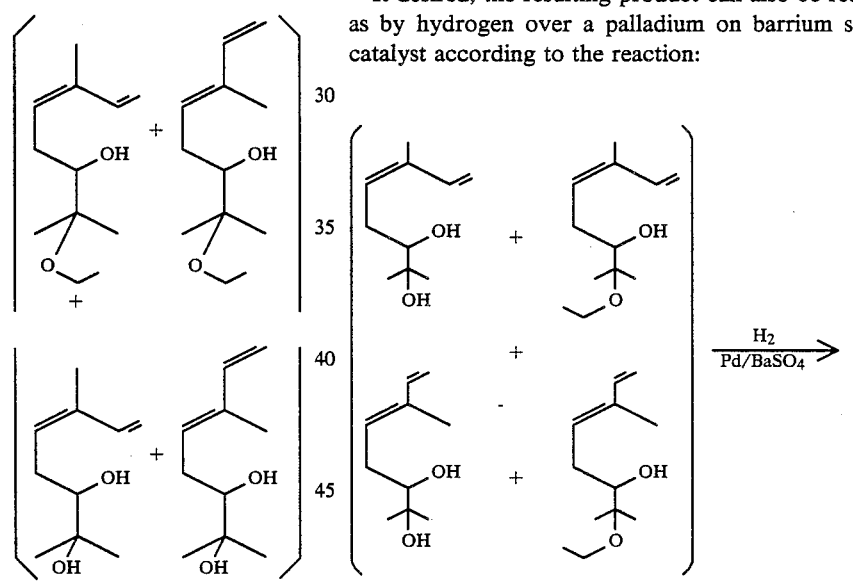
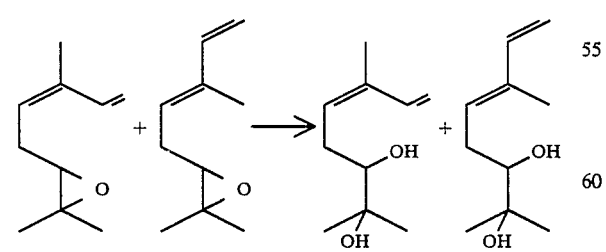
further, the resulting products can be oxidized to their corresponding ketones, for example, according to the reaction:
It desired, the resulting product can also be reduced as by hydrogen over a palladium on barrium sulfate catalyst according to the reaction:
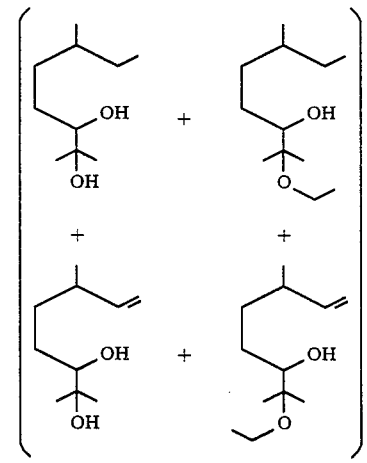

The present invention also provies a process for augmenting or enhancing the aroma of perfume compositions, colognes or perfumed articles by adding to such perfume compositions, colognes or perfumed articles at least one 3,7-dimethyl-6,7-dioxo-1,3-octadiene of our invention defined according to the structure:

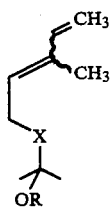

wherein R, X and the wavy lines are defined, supra. The perfumed articles of our invention include soaps, anionic, cationic, nonionic and zwitterionic detergents, fabric softener compositions, fabric softener articles, optical brightener compositions, perfumed polymers, hair preparations and the like. Accordingly, a need in the field of perfumery as well as in the field of perfumed articles and cosmetics manufacture, is fulfilled by augmenting or enhancing the specific aroma in such perfume compositions, colognes and perfumed articles, e.g., herbaceous, cut geranium stem, floral, fresh fruity, natural green and leafy aromas, with floral and citrusy topnotes and fruity, melony, peppery and citrusy undertones.

The 3,7-dimethyl-6,7-dioxo-1,3-octadienes of our invention can be prepared by means of reaction of the mixture of mycene epoxides defined according to the structures:

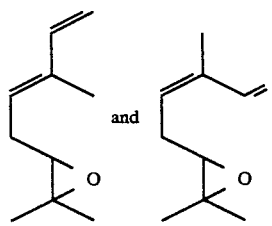

with or without ethanol in the presence of an acid catalyst according to one of the reactions:

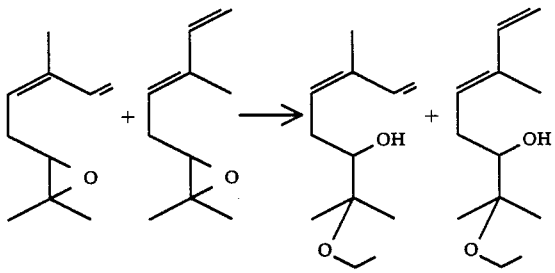

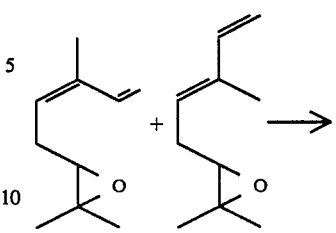

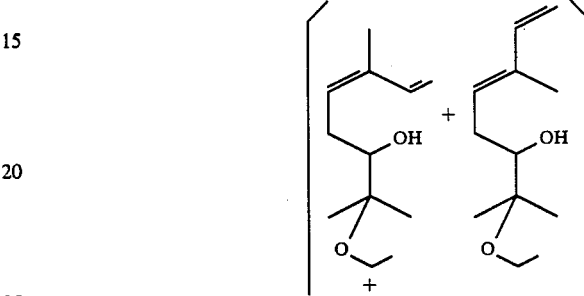

or

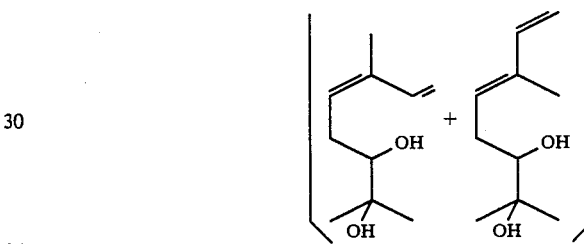

When the reaction is carried out in the presence of ethyl alcohol, the compounds having the structures:

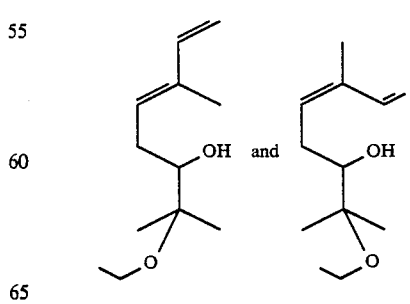

are produced (alone or further, together with the compounds having the structures:

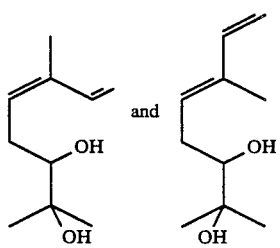

depending upon the conditions of reaction). When the reaction is carried out in the absence of ethyl alcohol, only the compounds having the structures:

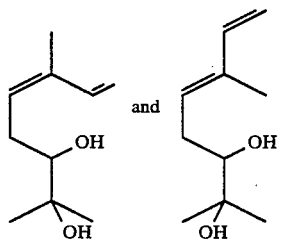

are produced.

Acid catalysts which may be used are as follows:
(a) acid ion exchange resins such as IR-120H, a sulfonated polystyrene resin;
(b) paratoluene sulfonic acid;
(c) phosphoric acid; and
(d) sulfuric acid.

The reaction, of course, is always carried out in the presence of water. The reaction is carried out preferably at ambient conditions, e.g., from about 20° up to about 40° C. and at about 1 atmosphere pressure.

At the end of the reaction, the reaction mass is fractionally distilled to yield odor acceptable fractions.

The resulting reaction products may be used "as is" or they may be further reacted as by hydrogenation or oxidation.

Thus, for example, when compounds having the structures:

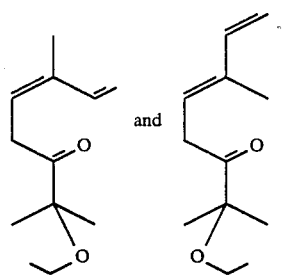

are desired, the compounds having the structures:

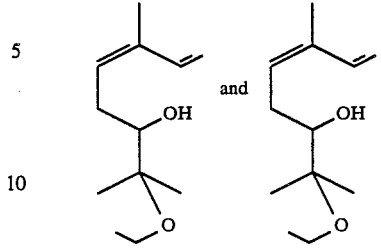

may be oxidized using standard oxidizing agents such as Jones reagent (a mixture of sodium dichromate and sulfuric acid) according to the reaction:

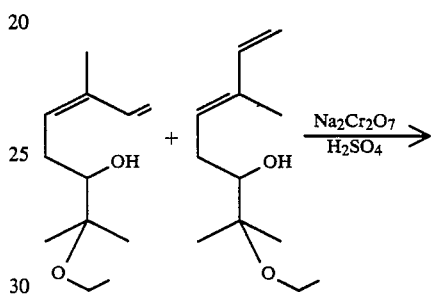

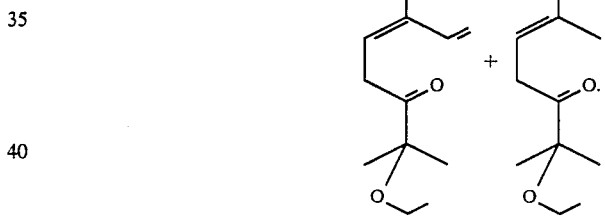

Furthermore, when compounds having the structures:

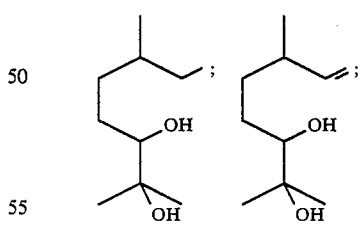

are desired, compounds having the structures:

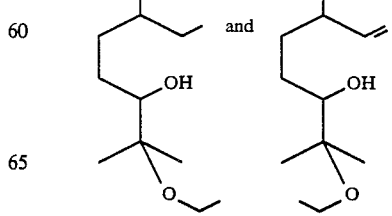

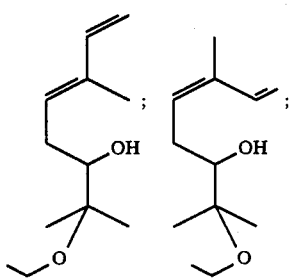

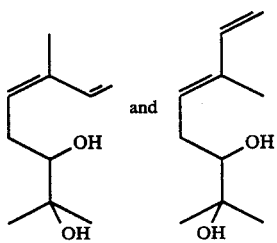

may be hydrogenated, for example, using hydrogen over a palladium on barium sulfate catalyst according to the reaction:

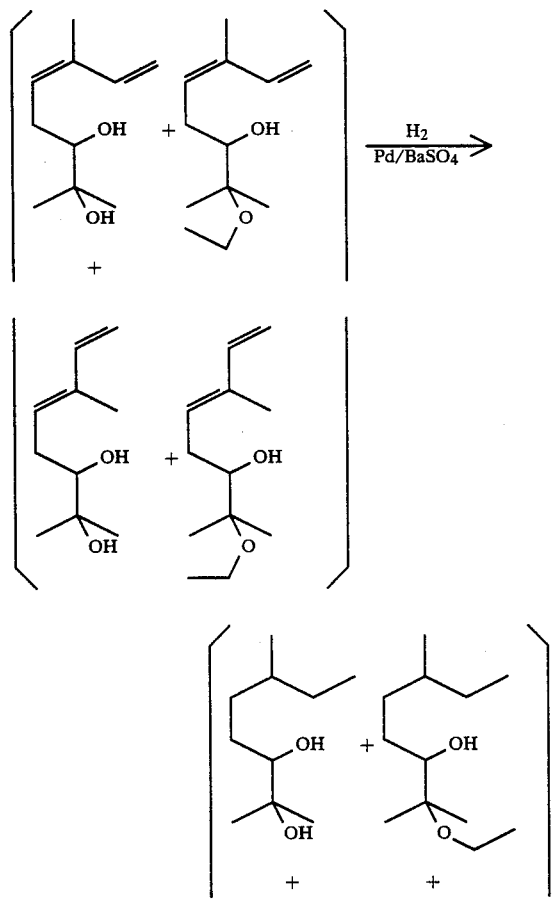

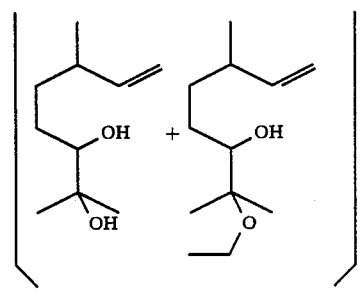

The following table lists the organoleptic properties and nature of reaction product which gives rise to such organoleptic properties.

TABLE I

| Structures of 3,7-Dimethyl-6,7-Dioxo-1,3-Octadienes | Organoleptic Properties |
|---|---|
| Mixture of compounds having the structures: [structures shown] prepared according to Example III. | A green, herbaceous, cut geranium stem aroma with floral and citrusy topnotes. |
| Mixture of compounds having the structures: [structures shown] prepared according to Example V(B). | A floral, fresh fruity, green and herbaceous aroma profile with floral and citrus topnotes. |
| The mixture of compounds having the structures: | An intense highly substantive tagette aroma profile. |

TABLE I-continued

| Structures of 3,7-Dimethyl-6,7-Dioxo-1,3-Octadienes | Organoleptic Properties |
|---|---|
| 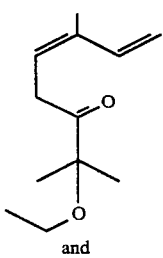 and 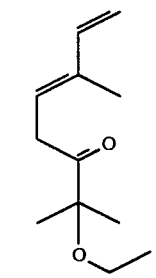 prepared according to Example VI. | |
| Mixture of compounds having the structures: 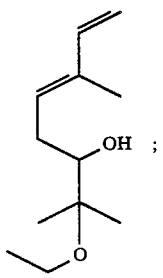 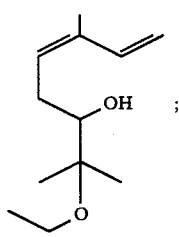 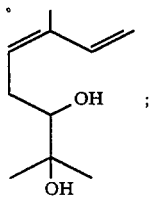 and 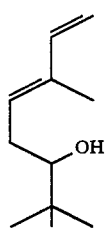 prepared according to Example VII. | A natural, green, leafy aroma with fruity, melony, peppery and citrusy undertones. |

At least one of the 3,7-dimethyl-6,7-dioxo-1,3-octadienes of our invention and one or more auxiliary perfume ingredients including, for example, alcohols other than the 3,7-dimethyl-6,7-dioxo-1,3-octadienes of our invention, ketones, aldehydes, terpenic hydrocarbons, nitriles, esters, lactones, ethers other than the 3,7-dimethyl-6,7-dioxo-1,3-octadienes of our invention, natural essential oils and synthetic essential oils may ne admixed so that the combined odors of the individual components produce a pleasant and desired fragrance, particularly and preferably in the fruity, green, herbaceous and floral fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, at least one of the 3,7-dimethyl-6,7-dioxo-1,3-octadienes of our inventionn can be used to alter, modify or enhance the aroma characteristics of a perfume composition, for example, by utilizing or moderating the olfactory reaction contributed by another ingredient in the composition.

The amount of at least one of the 3,7-dimethyl-6,7-dioxo-1,3-octadienes of our invention which will be effective in perfume compositions as well as perfumed articles (e.g., anionic, cationic, nonionic and zwitterionic detergents, soaps, fabric softener compositions, drier-added fabric softener articles, opticals brightener compositions, perfumed polymers, textile sizing agents and the like) and colognes depends on many factors, including the other ingredients, their amounts and the effects which are desired. It has been found that perfume compositions containing as little as 0.01% of one or more of the 3,7-dimethyl-6,7-dioxo-1,3-octadienes of our invention, or even less (e.g., 0.005%) can be used to impart, augment or enhance herbaceous, cut geranium stem, floral, fresh fruity, natural green and leafy aromas, with floral and citrusy topnotes and fruity, melony, peppery and citrusy undertones in or to soaps, cosmetics, solid or liquid anionic, cationic, nonionic and zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finishe product and the particular fragrance sought.

At least one of the 3,7-dimethyl-6,7-dioxo-1,3-octadienes of our invention is useful (taken alone or taken further together with other ingredients in perfume compositions) as (an) olfactory component(s) in detergents and soaps, space odorants and deodorants, perfumes, colognes, toilet water, bath preparations such as creams, deodorants, hand lotions and sun screens; powder, such as talcs, dusting powder, face powders and perfumed polymers and articles of manufacture produced from said perfumed polymers, e.g., garbage bags, children's toys and the like. When used as an olfactory components in perfumed articles, as little as 0.2% of at least one of the 3,7-dimethyl-6,7-dioxo-1,3-octadienes of our invention will suffice to impart, augment or enhance herbaceous, cut geranium stem, floral, fresh fruity, natural green and leafy aromas, with floral and citrusy topnotes and fruity, melony, peppery and citrusy undertones. Generally, no more than 6% of at least one of the 3,7-dimethyl-6,7-dioxo-1,3-octadienes of our invention based on the ultimate end prodduct is required in the perfumed article. Accordingly, the range of at least one of the 3,7-dimethyl-6,7-dioxo-1,3-octadienes of our invention in the perfumed article is from about 0.2% by weight of the 3,7-dimethyl-6,7-dioxo-1,3-octadienes up to about 6% by weight of the 3,7-dimethyl-6,7-dioxo-1,3-octadienes based on the total weight of the perfumed article.

In addition, the perfume composition or fragrance compositions of our invention can contain a vehicle or carrier for at least one of the 3,7-dimethyl-6,7-dioxo-1,3-octadienes of our invention. The vehicle can be liquid such as a non-toxic alcohol, e.g., ethyl alcohol, a non-toxic glycol, e.g., propylene glycol or the like. The carrier can be also an absorbetn solid, such as a gum (e.g., gum arabic, guar gum, xanthan gum or the like) or components for encapsulating the composition (such as, for example, gelatin as by coacervation or such as a urea formaldehyde prepolymer which on polymerization forms a capsule shell around the liquid perfume center).

Our invention also relates to the utlization of controlled release technology for the controlled release of perfumes into gaseous environments from polymers such as mixtures of epsilon polycaprolactone polymer and polyethylene which polyepsilon caprolactone polymers are defined according to at least one of the structures:

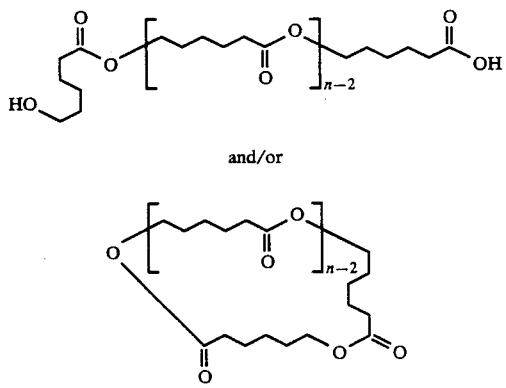

and/or wherein "n" is from about 50 up to about 1,200 with the proviso that the average "n" in the system varies from about 150 up to about 700 according to the mathematical statement:

$$[700 \geq \bar{n} \geq 150]$$

with the term $\bar{n}$
being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$dM_t/dt = k_1 e^{-k_2 t}$$

wherein $k_1$ and $k_2$ are constants. According to Kydonieus, "Controlled Release Technologies: Methods, Theory, and Applications" (cited, supra) the amount of perfume composition released is proportional to time as long as the concentration of perfume material present, e.g., at least one of the 3,7-dimethyl-6,7-dioxo-1,3-octadienes of our invention is higher than the solubility of the agent in the matrix. Thus, such dispersed systems are similar to the dissolved systems except that instead of a decreased release rate after 60% of the perfume material has been emmitted, the relationship holds almost over the complete release curve. Kydonieus further states, that if one assumes that the release of functional fluid by diffusion is negliglible in monolithic erodible systems, the speed of erosion will control the release rate and release by erosion by a surface-area-dependent phenomenon, the release being constant (zero order) as long as the surface area does not change during the erosion process. This is the case with polymers containing at least one of the 3,7-dimethyl-6,7-dioxo-1,3-octadienes of our invention.

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE THERMOPLASTIC POLYMERS PCL300 and PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is 300. Regarding PCL-700, the average number of repeating monomeric units is 700.

The polyepsilon carpolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilized the polyepsilon caprolactone useful in conjunction with our invention against discoloration are dihydroxybenzenes such hydroquinone or compounds having the formula:

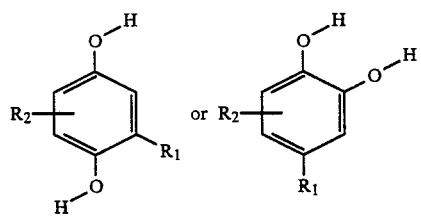

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfere with the functional fluids dissolved and/or absorbed into the polymeric matrix.

The method of incorporating at least one of the 3,7-dimethyl-6,7-dioxo-1,3-octadienes of our invention or perfume compositions containing same into the polymers may be according to the techniques of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylene-polyepsilon caprolactone polymer mixture (50:50) is mixed with at least one of the 3,7-dimethyl-6,7-dioxo-1,3-octadienes of our invention. Drops are formed from the mixture and the drops are then melted, if desired, with a second amount of unscented low density polyethylene, for example, or polypropylene, for example. Usually, but not necessarily, the second amount of polymer is larger than the first amount. The resulting mixture thus, obtained, is solidified subsequent to or prior to ultimate casting into a utilitarian shape.

Thus, in accordance with one aspect of our invention, the imparting of scent is effected in two stages. In a first stage a 50:50 (weight:weight) polyepsilon caprolactone, e.g., PCL-700: polyethylene in molten form is admixed with a high percentage of at least one of the 3,7-dimethyl-6,7-dioxo-1,3-octadienes of our invention and the mixture is solidified in the form of pellets or beads. These pellets or beads thus contain a high percentage of at least one of the 3,7-dimethyl-6,7-dioxo-1,3-octadienes (e.g., up to 45% by weight of the entire mixture) and may be used as "master pellets" which thereafter, in a second stage, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May. 7, 1981, the specification for which is incorporated by reference herein.

In accordance with the present invention, at least one of the 3,7-dimethyl-6,7-dioxo-1,3-octadienes of our invention is added to the polymer in a large closed container or drun which is maintained under controlled temperature conditions while the polymer in a melted condition is mixed with at least one of the 3,7-dimethyl-6,7-dioxo-1,3-octadienes under agitation.

In order that the perfume be added uniformly to the polymer, the temperature of the melt is constantly controlled during the process. The polymer-perfume mixture is then directed through an elongated conduit or pipe element having a plurality of orifices, adjacent to the lower most portion thereof. The polymer enriched by at least one of the 3,7-dimethyl-6,7-dioxo-1,3-octadienes of our invention is permitted to drip through the orifices onto a continuously moving, cooled conveyor upon which the polymer containing at least one of the 3,7-dimethyl-6,7-dioxo-1,3-octadienes of our invention solidifies into small size pellets with the perfume imprisoned therein. The apparatus useful in conjunction with this process, advantageously includes a conveyor of a material which will not adhere to the polymer which contains at least one of the 3,7-dimethyl-6,7-dioxo-1,3-octadienes of our invention.

In order that the droplets form into uniform pellets or beads, the conveyor is continuously washed with a liquid, such as water to maintain the surface relatively cool. The pellets are delivered by the conveyor into a container and packaged for shipment.

The following Examples I–IX illustrates processes for preparing the 3,7-dimethyl-6,7-dioxo-1,3-octadienes of our invention as well as compounds of the prior art. Examples following Example IX are illustrative of the organoleptic utilites of the 3,7-dimethyl-6,7-dioxo-1,3-octadienes of our invention.

All parts and percentages given herein are by weight unless otherwise specified.

EXAMPLE I

Steam Distillation and Analysis of Marigold Absolute

To a 3 neck 1,000 ml reaction flask equipped with a 500 ml distilled water steam generator, pot thermometer, rush over head, including thermometer, fraction collector, vacuum gauge, vacuum pump, 2 dry ice traps and a heating mantle, was added to the reaction flask 175.0 grams of marigold absolute and 150 ml distilled water.

20 mm Vacuum was applied to the system and steam was passed through the 3 neck 500 ml reaction flask via the distilled water steam generator.

The distillation was continued for a period of two hours at about 45°–50° C. and reduced pressure (20 mm/Hg).

The resulting steam distillate (17.5 grams) was then separated into its neutral, acidic, basic and phenolic parts by group separation procedures as shown in the following tables:

TABLE II

Steam Distilled Marigold Oil 17.0 Grams
Dissolved In 200 Ml of Diethyl Ether

| Extract (3x) with 5% NaHCO₃ (75 ml portions) | Extract (3x) with 5% Na₂CO₃ (75 ml portions) | Extract (2x) with 5% NaOH (50 ml portions) | Extract (3x) with 10% HCl (50 ml portions) |
|---|---|---|---|
| Ether extract Aqueous 5x (50 ml portions) | Ether extract Aqueous 5x (50 ml portions) | Ether extract Aqueous 5x (50 ml portions) | Extract Aqueous 5x with Ether (50 ml portions) |
| Acidify (10% HCl) to a pH of 2 | Acidify (10% HCl) to a pH of 2 | Acidify (10% HCL) to a pH of 2 | Make basic with C or NH₄OH to pH of 12 |
| Extract 3x with Ether; Dry (MgSO₄) | Extract 3x with Ether Dry (MgSO₄) | Extract 3x with Ether Dry (MgSO₄) | Ether Extract 3x, dry(MGSO₄) |
| Remove Solvent Under Reduced Pressure | Remove solvent Under Reduced Pressure | Remove solvent Under Reduced Pressure | Remove Solvent Under Reduced Pressure |
| LOWER ACIDS 0.15 grams Analyze by GC/MS | HIGHER ACIDS 0.3 grams Analyze by GC/MS | PHENOLS 0.15 grams Analyze by GC/MS | BASES 0.1 grams Analyze by GC/MS |

TABLE II-continued

Steam Distilled Marigold Oil 17.0 Grams
Dissolved In 200 Ml of Diethyl Ether

Ether layer wash
neutral with water
Dry - Remove
Solvent 15.3 NEUTRAL.

The pot residue from the steam distillation was then separated into its group parts and analyzed by GC/MS.

TABLE III

Pot Residue of Steam Distillation 155.0 Grams
Dissolved In 300 ml Diethyl Ether

| Extract Ether Layer with 5% NAOH 2x 50 Ml Portions Extract Aqueous 5 x With Ether Acidify With 10% HCl Extract Aqueous 2 x With Ether Dry (MgSO4) Remove Solvent At Reduced Pressure | Extract 3 x With 5% Na2CO3 Extract Aqueous 5 x With Ether Acidify 10% HCl Extract Aqueous 2 x Ether Dry (MgSO4) Remove Solvent At Reduced Pressure | Extract Ether Layer With 10% HCl 3 x 50 Ml Portions Extract Aqueous 5 x With Ether 50 Ml Portions Make Basic With Con. NH4OH To a pH of 12 Extract 2 x With Ether (Aqueous) Dry, (MgSO4) Remove Solvent At Reduced Pressure |
|---|---|---|
| PHENOLS of Steam Distillate Residue Weight = 0.30 grams | Acids of Steam Distillate Residue Weight = 9.00 grams | |
| | | BASES of Steam Distillate Residue Weight = 0.06 grams |

THE ANALYSIS

Marigold Absolute Steam Distillate

1. Volatiles = 10%
   Acid Fraction = 2.57%
   Basic Fraction = 0.57%
   Phenolic Fraction = 0.90%
   Neutral Fraction = 94.96%
2. Non-Volatile = 90%
3. Headspace Fraction = 1.00%

| COMPOUND IDENTIFIED | PERCENT |
|---|---|
| NEUTRALS OF MARIGOLD | |
| 3-Hexanol | 0.01 |
| 2-Hexanol | 0.01 |
| Cis-3-Hexenol | 0.07 |
| Trans-2-Hexenol | 0.05 |
| N-Hexanol | 0.09 |
| Isoamyl Acetate | 0.01 |
| 2-Heptanol | 0.01 |
| Benzaldehyde | 0.01 |
| 6-Methyl-5-Hepten-2-One | 0.01 |
| Sabinene | 0.01 |
| Myrcene | 1.00 |
| Cis-3-Hexenyl Acetate | 0.11 |
| N-Hexyl Acetate | 0.06 |
| Methyl Anisole | 0.07 |
| Benzyl Alcohol | 0.11 |
| P-Cymene | 0.03 |
| Limonene | 1.00 |
| Ocimene | 11.20 |
| Dihydro Tagetone | 6.00 |
| Phellandrene | 0.09 |
| Methyl Benzoate | 0.06 |
| Alpha-Dimethyl Styrene | 0.80 |
| Terpinolene | 3.90 |
| Phenyl Ethyl Alcohol | 0.50 |
| Linalool | 1.00 |
| Methyl Acetophenone | 0.08 |
| Perillen | 0.05 |
| Myroxide | 6.80 |
| Camphor | 0.30 |
| Tagetone | 1.60 |
| Benzyl Acetate | 2.50 |
| Borneol | 0.05 |
| 1,8-Cineole | 0.90 |
| Cis-3-Hexenyl Iso Butyrate | 1.50 |
| Alpha-Terpineol | 1.00 |
| Ethyl Octanoate | 0.20 |
| 2,6-Dimethyl-1,5,7-Octatriene-3-ol | 0.05 |
| Carveol | Trace |
| Citronellol | 0.05 |
| 8-Cymenyl Ethyl Ether | 0.05 |
| Phenyl Ethyl Acetate | 1.00 |
| Benzyl Propionate | 0.91 |
| Borneol Acetate | 0.05 |
| Mixture of compounds having the structures: | 3.20 |

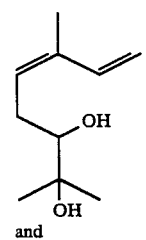

and

-continued

| COMPOUND IDENTIFIED | PERCENT |
|---|---|

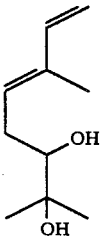

| | |
|---|---|
| Piperitenone | 11.70 |
| Mixture of Compounds having the structures: | 3.50 |

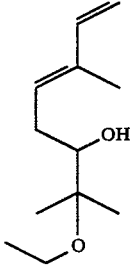

and

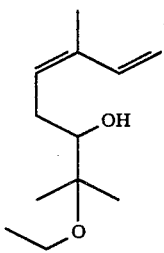

| | |
|---|---|
| Ethyl Dodecanoate | 0.50 |
| Caryophyllene | 20.10 |
| Alpha-Humulene | 0.30 |
| Beta-Cubebene | 2.20 |
| Alpha-Elemene | 0.30 |
| Alpha-Farnesene | 0.30 |
| Cardina-3,9-Diene | 0.30 |
| Diethyl Phthalate | 0.10 |
| Caryophyllene Oxide | 0.80 |
| Ethyl Tetradecanoate | 0.20 |
| Benzyl Benzoate | 0.20 |
| | 87.00 |

DRY ICE TRAP OF STEAM DISTILLATION OF MARIGOLD ABSOLUTE

| | |
|---|---|
| Ethyl Acetate | 0.05 |
| Isopropyl Alcohol | 0.01 |
| Cis-3-Hexenol | 0.07 |
| Trans-2-Hexenol | 0.13 |
| 2-Heptanol | 0.01 |
| 2-Buten-1-ol, 3 Methyl Acetate | 0.02 |
| Benzaldehyde | 0.02 |
| Sabinene | 0.24 |
| Myrcene | 2.14 |
| Cis-3-Hexenyl Acetate | 0.24 |
| N-Hexyl Acetate | 0.08 |
| Methyl Anisole | 0.16 |
| Para Cymene | 0.02 |
| Limonene | 2.69 |
| Cis-Ocimene | 17.30 |
| Dihydro Tagetone | 9.10 |
| Trans-Ocimene | 3.00 |
| Beta-Phellendrene | 0.02 |
| 2-Methyl-5-Isopropyl Furan | 0.04 |
| Methyl Benzoate | 0.08 |
| Alpha-Para Dimethyl Styrene | 0.90 |
| Terpinolene | 8.19 |
| Linalool | 1.00 |

-continued

| COMPOUND IDENTIFIED | PERCENT |
|---|---|
| Methyl Acetophenone | 0.43 |
| Perillen | 0.15 |
| Cis-Ocimene Epoxide | 8.20 |
| Camphor | 0.50 |
| Trans-Ocimene | 13.05 |
| Tagetone | 0.80 |
| Benzyl Acetate | 2.00 |
| Ethyl Benzoate | 0.01 |
| Borneol | 0.02 |
| Alpha-Terpineol | 0.19 |
| Cis-3-Hexenyl Isobutyrate | 1.60 |
| Ethyl Octanoate | 0.43 |
| Benzyl Propionate | 0.53 |
| Iso Piperitenone | 0.01 |
| Mixture of Compounds having the structures: | 0.31 |

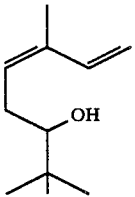

and

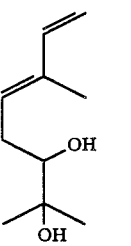

| | |
|---|---|
| Piperitenone | 2.30 |
| Mixture of Compounds having the structures: | 0.54 |

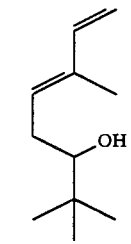

and

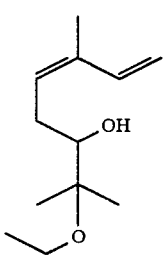

| | |
|---|---|
| Ethyl Decanoate | 0.09 |
| Beta-Caryophyllene | 16.10 |
| Alpha-Humulene | 0.27 |
| Beta-Cubebene | 1.40 |
| Alpha-Elemene | 0.41 |
| Alpha-Farnesene | 0.10 |
| Delta-Cadinene | 0.10 |
| | 95.05 |

LOWER ACIDS OF MARIGOLD ABSOLUTE

-continued

| COMPOUND IDENTIFIED | PERCENT |
|---|---|
| (NaHCO3 Extract of Marigold Steam Distillate) Weight of Extract = 0.15 Grams - % of Extract = 0.15 | |
| Isovaleric Acid | 0.90 |
| Valeric Acid | 1.75 |
| Hexanoic Acid | 7.15 |
| Heptanoic Acid | 1.45 |
| Octanoic Acid | 69.42 |
| Nonanoic Acid | 2.07 |
| Geranic Acid | 0.70 |
| Decanoic Acid | 9.00 |
| Cinnamic Acid | 0.90 |
| Jasmine Lactone | 0.10 |
| Ionol | 0.05 |
| 2,5-Diisobutylthiophene | 0.05 |
| Diethylphthalate | 0.08 |
| 2,6-Ditertbutyl-4-Ethyl Phenol | 0.03 |
| Dipropyl Phthalate | 0.09 |
| Hexadecanoic Acid | 0.10 |
| Di(2-Ethylhexyl) Phthalate | 0.02 |
| | 93.86 |

HIGHER ACIDS OF MARIGOLD ABSOLUTE
(Na2CO3 Extract of Marigold Steam Distillate)
Weight of Extract = 0.3 Grams - % of Extract = 0.3

| Octanoic Acid | 0.10 |
|---|---|
| Eugenol | 1.00 |
| Decanoic Acid | 21.90 |
| Vanillic Acid Methyl Ester | 0.20 |
| Ionol | 0.10 |
| Dodecanoic Acid | 9.40 |
| Tridecanoic Acid | 0.20 |
| Tetradecanoic Acid | 12.50 |
| Pentadecanoic Acid | 0.30 |
| Hexadecanoic Acid | 35.00 |
| Veg Acid 1520 | 17.75 |
| Octadecanoic Acid | 1.00 |
| | 99.45 |

PHENOLS OF MARIGOLD ABSOLUTE
(NaOH Extract of Marigold Steam Distillate)
Weight of Extract = 0.15 Grams - % of Extract = 0.15

| Phenol | 1.60 |
|---|---|
| Para Cresol | 1.40 |
| Guaiacol | 5.00 |
| 4-Ethyl Phenol | 0.60 |
| 2-Methoxy-4-Methyl Phenol | 0.23 |
| Phthalic Anhydride | Trace |
| Vinyl Guaiacol | 0.20 |
| Salicylic Acid | 4.02 |
| Eugenol | 80.43 |
| 3-Hydroxy P-Anisic Aldehyde | 0.42 |
| Jasmine Lactone | 0.23 |
| Ionol | 1.00 |
| | 95.13 |

BASES OF MARIGOLD ABSOLUTE
(HCl Extract of Marigold Steam Distillate)
Weight of Extract = 0.10 Grams - % of Extract = 0.10

| 2-Methoxy-3-Isopropyl 5-Methyl Pyrazine | Trace |
|---|---|
| 1,8-Cymenol | 17.10 |
| Methyl Anthranilate | 53.00 |
| Ionol | 3.63 |
| Benzothiazole | Trace |
| | 73.73 |

ACIDS OF MARIGOLD STEAM DISTILLATE RESIDUE
Acid Fraction = 9.00 Grams

| Heptanoic Acid | 0.5 |
|---|---|
| Octanoic Acid | 8.0 |
| Nonanoic Acid | 0.5 |
| Decanoic Acid | 15.0 |
| Dodecanoic Acid | 5.0 |
| Myristic Acid | 9.0 |
| Pentadecanoic Acid | 1.0 |
| Hexadecanoic Acid | 25.0 |
| Octadecanoic Acid | 5.0 |
| Cinnamic Acid | 7.0 |
| Azelaic Acid | 3.0 |
| Veg Acid 1520 | 7.0 |
| | 86.00 |

BASES OF MARIGOLD STEAM DISTILLATE RESIDUE

-continued

| COMPOUND IDENTIFIED | PERCENT |
|---|---|
| Basic Fraction = 0.06 Grams | |
| 1,8-Cymenol | 5.00 |
| Benzothiazole | 0.10 |
| Borneol | 3.00 |
| Isoborneol | 5.00 |
| Methyl Anthranilate | 32.40 |
| Ionol | 39.23 |
| | 84.73 |

PHENOLS OF MARIGOLD STEAM DISTILLATE RESIDUE
Phenolic Fraction = 0.30 Grams

| Eugenol | 95.00 |
|---|---|
| Ionol | 1.00 |
| Ferulic Acid | 1.00 |
| | 97.00 |

FIG. 1 is the GLC profile of the neutrals of the steam distillate of marigold absolute (Conditions: 50 M×0.32 mm OV-1 column programmed at 60°–220° C. at 2° C. per minute). The peak indicated by reference numeral 14 is the peak for cis-ocimene. The peak indicated by reference numeral 16 is the peak for dihyrotagetone. The peak indicated by reference numeral 18 is the peak for transicimene epoxide. The peaks indicated by reference numerals 11 and 13 are the peaks for the compounds having the structures:

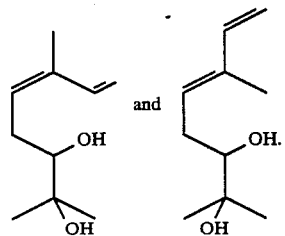

The peaks indicated by reference numerals 10 and 12 are the peaks for the compounds having the structures:

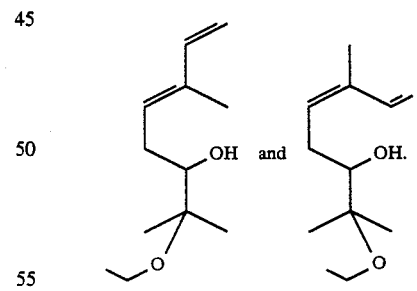

The peak indicated by reference numeral 19 is the peak for caryophyllene. Other peaks on this GLC profile include beta-phallandrene, myrcene, alpha-elemene, alpha-pharnacene, ethyl tetradecanoate and benzyl benzoate, interalia.

EXAMPLE II

Acid Treatment of Myroxide

Reaction:

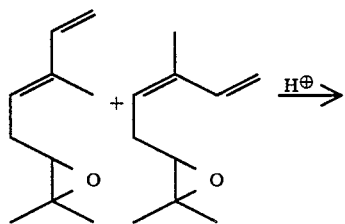

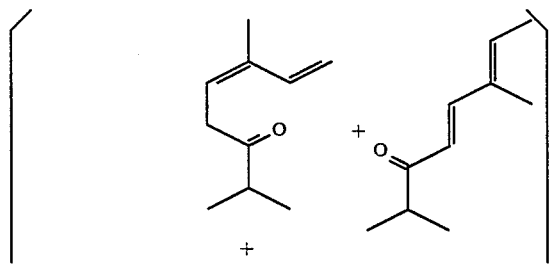

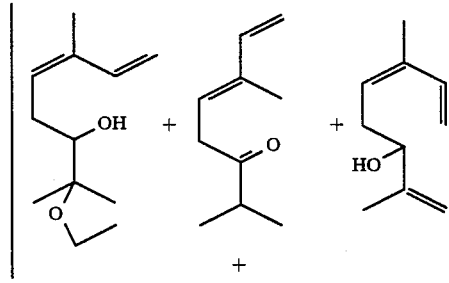

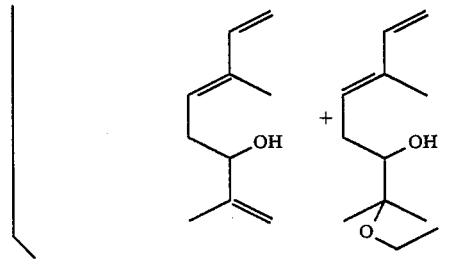

Into a 100 ml receiver was added two grams of myroxide, a mixture of compounds having the structures:

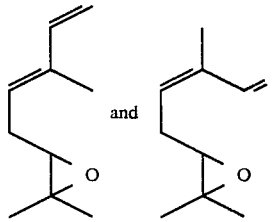

and 20 ml absolute ethanol. IR-120H (polystyrene sulfonate) ion exchange resin (0.2 grams) was added and the mixture was stirred vigorously at room temperature. After three hours the reaction was complete (as shown by GLC).

The resin was filtered off and 10 ml of saturated salt water and 20 ml diethyl ether was added to the ethanol layer. The layers were separated and the ether layer was washed with three 25 ml portions of distilled water. After drying over anhydrous magnesium sulfate and solvent removal, 1.9 grams of crude material resulted.

The resultant crude material was distilled on a micro rush over still yielding four fractions. These fractions were as follows:

| Fraction No. | Vapor Temp. (°C.) | Liquid Temp. (°C.) | Vacuum mm/Hg. Pressure |
|---|---|---|---|
| 1 | 37/43 | 63/64 | 3.0/3.0 |
| 2 | 60 | 68 | 3.0 |
| 3 | 67 | 73 | 3.0 |
| 4 | 70 | 82 | 3.0. |

FIG. 2 is the GLC profile for the crude reaction product of Example II (Conditions: OV-1 column programmed at 80°-200° C. at 4° C. per minute). The peak indicated by reference numeral 21 is the peak for the compound having the structure:

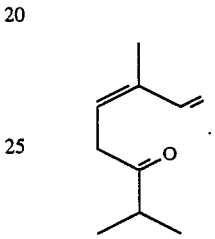

The peak indicated by reference numeral 22 is the peak for the compound having the structure:

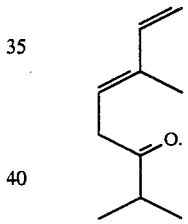

The peak indicated by reference numeral 23 is the peak for the compound having the structure:

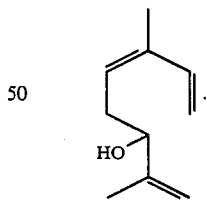

The peak indicated by reference numeral 24 is the peak for the compound having the structure:

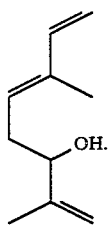

The peak indicated by reference numeral 25 is the peak for the compound having the structure:

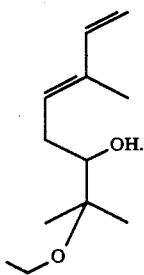

The peak indicated by reference numeral 26 is the peak for the compound having the structure:

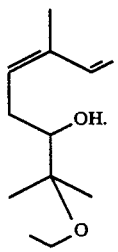

FIG. 3 is the GLC profile for distillation fraction 2 of the distillation of the reaction product of Example II (Conditions: OV-1 column programmed at 80°–220° C. at 4° C. per minute). The peak indicated by reference numeral 31 is the peak for the compound having the structure:

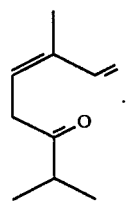

The peak indicated by reference numeral 32 is the peak for the compound having the structure:

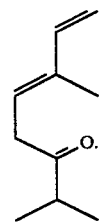

The peak indicated by reference numeral 33 is the peak for the compound having the structure:

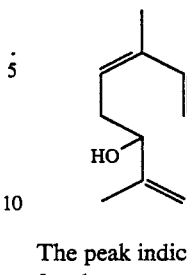

The peak indicated by reference numeral 34 is the peak for the compound having the structure:

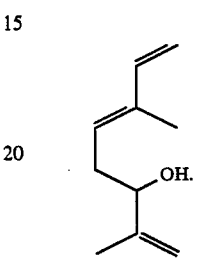

Figure 4:
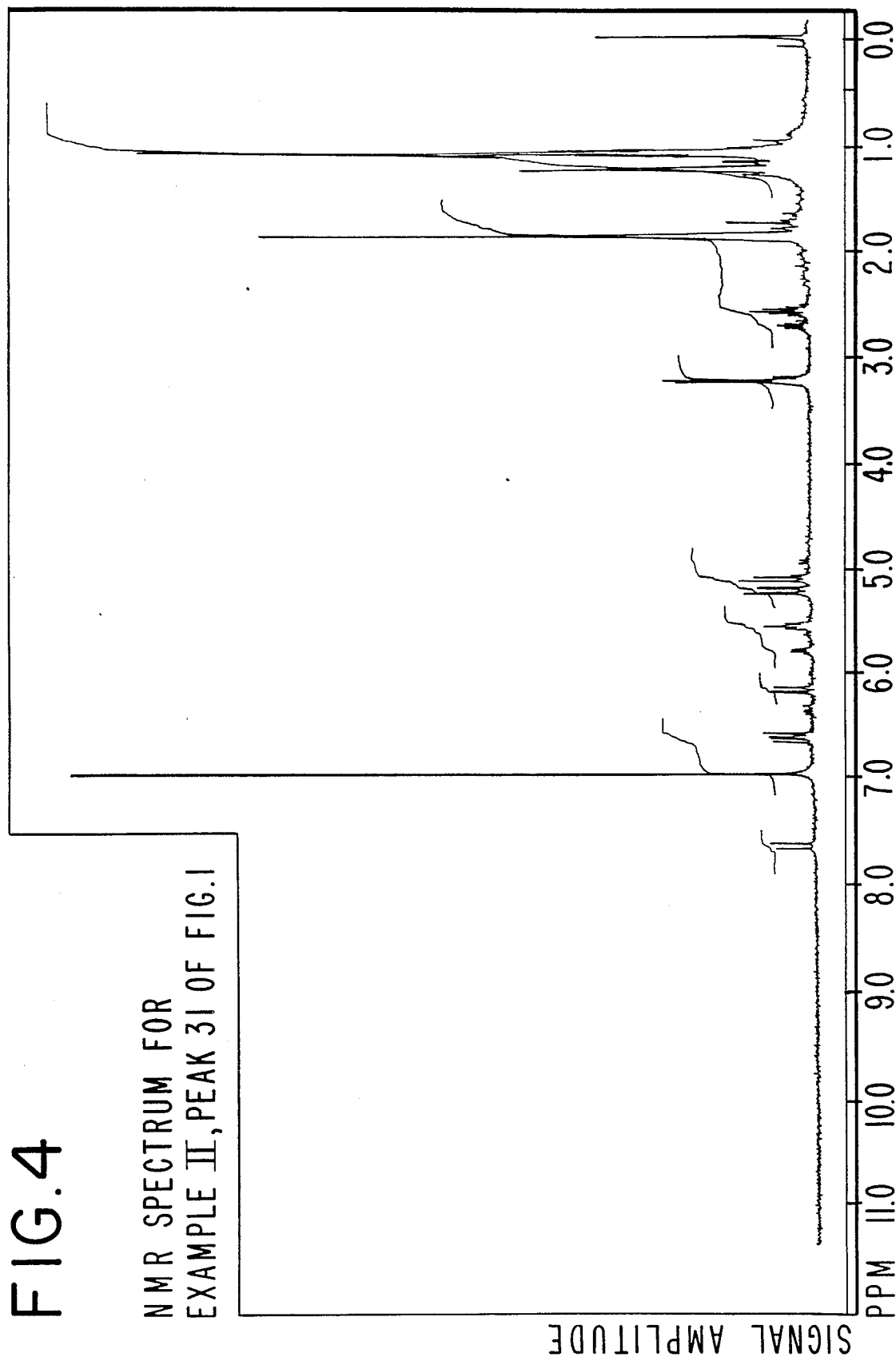
FIG. 4 is the NMR spectrum for the peak indicated by reference numeral 31 of FIG. 3, the GLC profile containing the compounds having the structures.

FIG. 4 is the NMR spectrum for the peak indicated by reference numeral 31 of FIG. 3, the GLC profile containing the compounds having the structures:

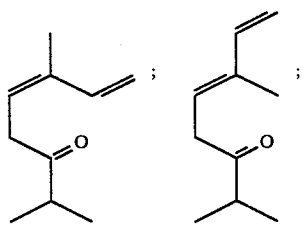

and 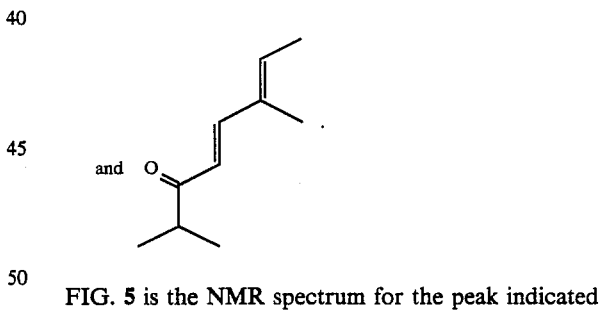

FIG. 5 is the NMR spectrum for the peak indicated by reference numeral 32 of FIG. 3 for the compound having the structure:

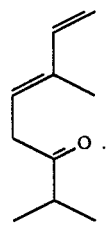

FIG. 6 is the NMR spectrum for the peak indicated by reference numeral 33 of the GLC profile of FIG. 3 (Example II) for the compound having the structure:

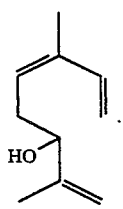

FIG. 7 is the NMR spectrum for the peak indicated by reference numeral 34 of the GLC profile of FIG. 3 (Example II) for the compound having the structure:

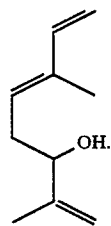

FIG. 8 is the NMR spectrum for the peak indicated by reference numeral 26 of FIG. 2 for the compound having the structure:

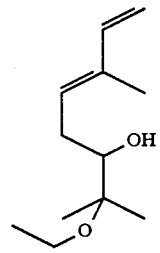

(Example II).

EXAMPLE III

Reaction of Myroxide Using Para Toluene Sulfonic Acid

Reaction:

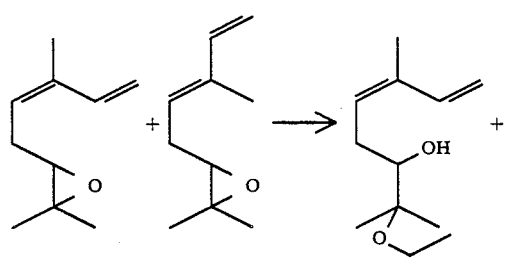

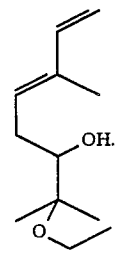

To a 125 ml reaction vessel was added 20 grams of myroxide, 50 ml of anhydrous ethyl alcohol and 0.2 grams para toluene sulfonic acid.

The mixture was stirred for a period of 24 hours. GLC analysis showed the starting material had completely reacted to form two new products. The mixture was then diluted with 50 ml saturated salt and the layers separated. The aqueous layer was extracted with two volumes of 30 ml diethyl ether. The diethyl ether extracts were added to the organic layer and the resulting material was then washed with two volumes (30 ml each) saturated sodium bicarbonate solution followed by two volumes (30 ml each) of distilled water.

After drying and evaporation of solvent 20.0 grams of crude product resulted. Distillation resulted in ten fractions as follows:

| Fraction No. | Vapor Temp. (°C.) | Liquid Temp. (°C.) | Vacuum mm/Hg. Pressure |
|---|---|---|---|
| 1 | 61/87 | 97/103 | 5.0/5.0 |
| 2 | 90 | 104 | 5.0 |
| 3 | 75 | 96 | 5.0 |
| 4 | 83 | 100 | 2.5 |
| 5 | 85 | 103 | 2.5 |
| 6 | 87 | 105 | 3.5 |
| 7 | 87 | 108 | 3.0 |
| 8 | 86 | 108 | 3.0 |
| 9 | 82 | 106 | 2.8 |
| 10 | 74 | 121 | 2.6 |
| 11 | 40 | 150 | 2.5. |

FIG. 9 is the GLC profile for the crude reaction product of Example III (Conditions: Fused silica OV-1 column programmed at 60°-220° C. at 2° C. per minute). The peaks indicated by reference numerals 90 and 92 are the peaks for the compounds having the structures:

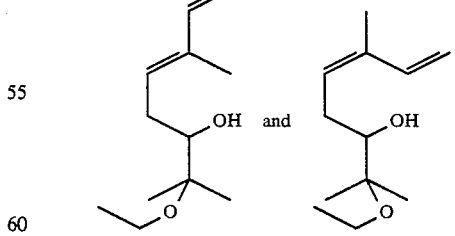

(ratio: 34.2:39.2).

An upscaled version of the foregoing experiment was run to obtain more product. 50 Grams of myroxide, 120 ml anhydrous ethyl alcohol and 0.5 grams of para toluene sulfonic acid were used. The product work up was the same as set forth, supra. Distillation however yielded 11 fractions.

FIG. 10 is the GLC profile for distillation fraction 11 of the distillation of the reaction product of Example III (Conditions: OV-1 column programmed at 60°-220° C. at 2° C. per minute). The peaks indicated by reference numerals 101 and 103 are the peaks for the compounds having the structures:

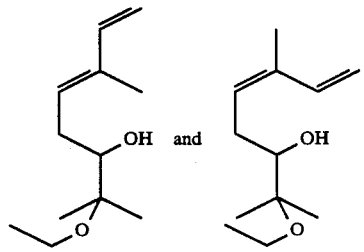

(ratio: 43.5:38).

FIG. 11 is the NMR spectrum for distillation fraction 11 of the distillation of the reaction product of Example III containing the compounds having the structures:

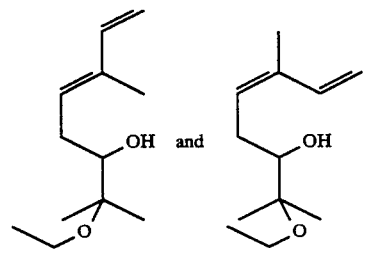

FIG. 12 is the NMR spectrum for the acetylated fraction 11 of the distillation of the reaction product of Example III containing the compounds having the structures:

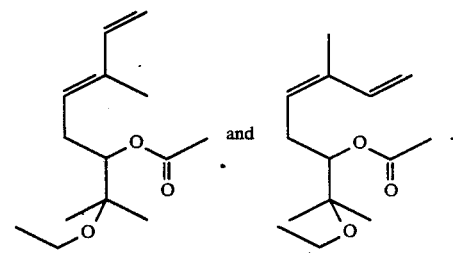

EXAMPLE IV

Acidification of Myroxide Using Para Toluene Sulfonic Acid and 90% Ethyl Alcohol and 10% Water Reaction:

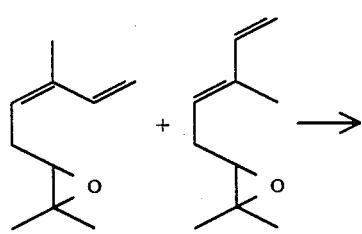

-continued

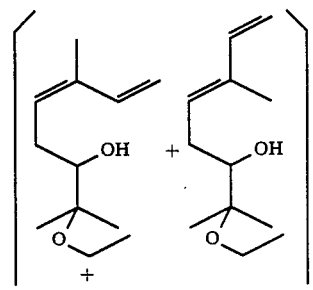

To a 125 ml reaction vessel was added 20 grams of myroxide, 45 ml anhydrous ethanol and 5 grams water with 0.3 grams para toluene sulfonic acid. The mixture was stirred 5 hours and analyzed by GLC which showed an equal mixture of compounds having the structures:

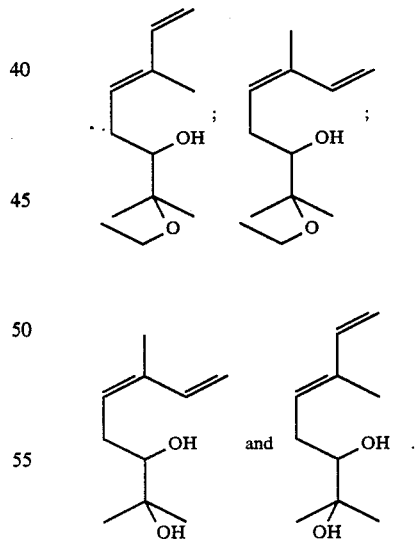

This material was not worked up.

FIG. 13 is the GLC profile for the crude reaction product of Example IV (Conditions: OV-1 column programmed at 60°-220° C. at 4° C. per minute). The peaks indicated by reference numerals 130 and 132 are the peaks for the compounds having the structures:

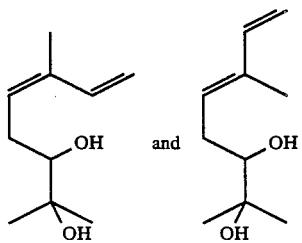

(ratio: 24:27). The peaks indicated by reference numerals 134 and 136 are the peaks for the compounds having the structures:

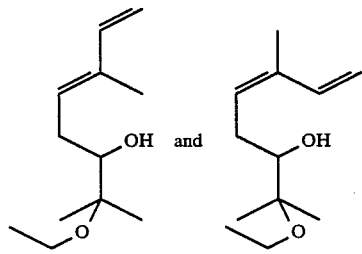

(ratio: 16:29).

EXAMPLE V(A)

Reaction of Myroxide Using Para Toluene Sulfonic Acid and a 50:50 Ethanol Water Mixture Reaction:

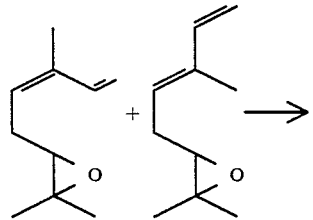

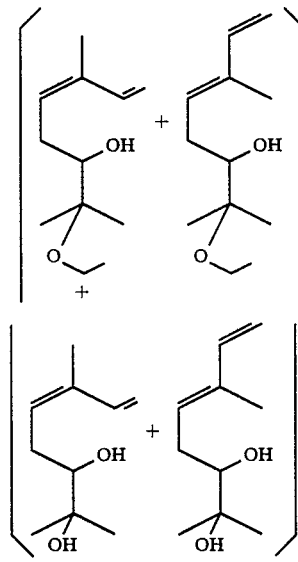

To a 125 ml reaction vessel was added 20 grams of myroxide, 25 ml anhydrous ethanol, 25 ml distilled water and 0.3 grams para toluene sulfonic acid. The reaction mixture was stirred for a period of 24 hours at room temperature. After usual work up with isolation of the organic layer, washing with 10% sodium bicarbonate solution, water, drying and evaporation of solvent 19.7 grams of crude reaction product resulted.

Distillation yielded 8 fractions as follows:

| Fraction No. | Vapor Temp. (°C.) | Liquid Temp. (°C.) | Vacuum mm/Hg. Pressure |
|---|---|---|---|
| 1 | 40/55 | 90/96 | 3.0/3.0 |
| 2 | 66 | 100 | 3.0 |
| 3 | 71 | 102 | 3.0 |
| 4 | 84 | 105 | 3.0 |
| 5 | 84 | 106 | 3.0 |
| 6 | 84 | 113 | 3.0 |
| 7 | 65 | 135 | 2.0 |
| 8 | 40 | 160 | 2.0. |

FIG. 14 is the GLC profile for the crude reaction product of Example V(A) (Conditions: 50M×0.32 mm fused silica OV-1 column programmed at 60°-220° C. at 4° C. per minute). The peaks indicated by reference numerals 140 and 142 are for the compounds having the structures:

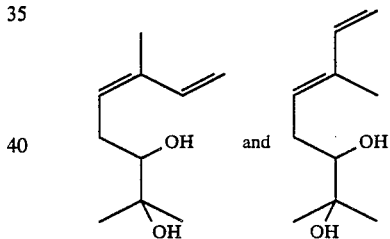

(35.0% and 40% of reaction product). The peaks indicated by reference numerals 144 and 146 are the peaks for the compounds having the structures:

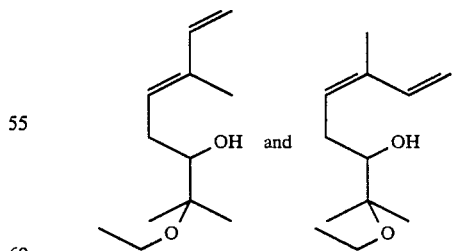

(7.3 and 7.8% of the reaction product).

EXAMPLE V(B)

Reaction of Myroxide with Para Toluene Sulfonic Acid and Water

Reaction:

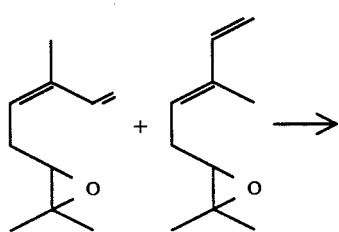

+ →

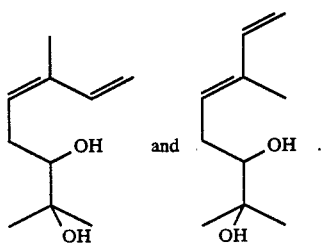

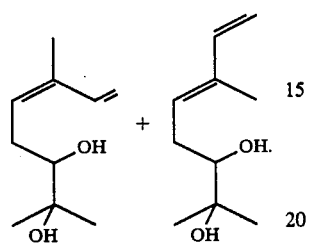

To a 125 ml reaction vessel was added 20 grams of myroxide, 25 ml distilled water and 0.15 grams of para toluene sulfonic acid. This mixture was then stirred vigorously at room temperature for 20 hours. The layers were then separated and the organic layer was diluted with diethyl ether (75 ml) and washed two times with 10% sodium bicarbonate solution (30 ml portions) followed by two water portions (30 ml each). The organic material was dried over anhydrous magnesium sulfate and the solvent removed. 18.5 Grams of crude product was obtained and yielded 5 fractions on distillation as follows:

| Fraction No. | Vapor Temp. (°C.) | Liquid Temp. (°C.) | Vacuum mm/Hg. Pressure |
|---|---|---|---|
| 1 | 40/55 | 90/96 | 3.0/3.0 |
| 2 | 66 | 100 | 3.0 |
| 3 | 71 | 102 | 3.0 |
| 4 | 84 | 105 | 3.0 |
| 5 | 106 | 60 | 3.0 |
| 6 | 84 | 113 | 3.0 |
| 7 | 65 | 135 | 2.0 |
| 8 | 40 | 160 | 2.0. |

FIG. 15 is the GLC profile for the crude reaction product of Example V(B) (Conditions: 50M×0.32 mm fused silica OV-1 column programmed at 60°-220° C. at 4° C. per minute). The peaks indicated by reference numerals 151 and 153 are for the compounds having the structures:

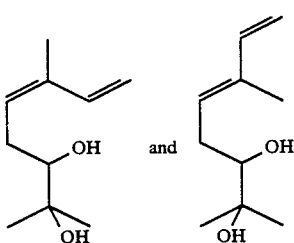

(ratio: 38:44).

FIG. 16 is the NMR spectrum for distillation fraction 4 of the distillation of the reaction product of Example V(B) containing the compounds having the structures:

EXAMPLE VI

Syntheses of
2-Ethoxy-2,6-Dimethyl-5,7-Octadien-3-One

Reaction:

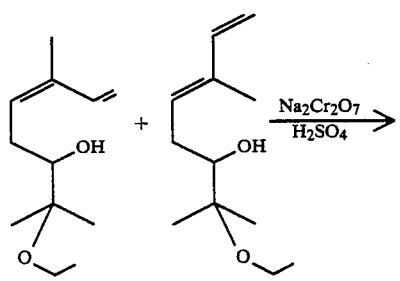

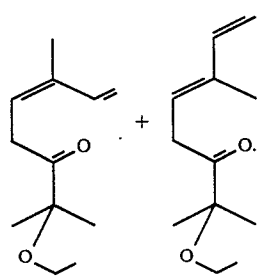

Into a 3 neck 250 round bottom flask equipped with stirrer, thermometer, condenser and addition funnel is charged 10 grams of the mixture of compounds having the structures:

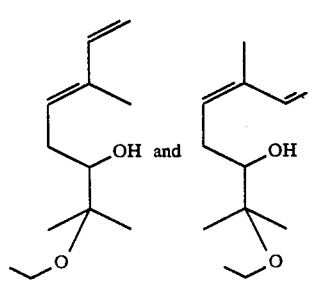

prepared according to Example III and 20 ml diethyl ether.

Separately, a "Jones Reagent" solution is prepared by mixing 5 grams of sodium dichromate monohydrate and 3.75 ml concentrated sulfuric acid and diluting to 25 ml with water.

The "Jones Reagent" solution is added dropwise over a period of 20 minutes to the reaction vessel while cooling the reaction vessel to a temperature of 18° C.

The reaction mass is then allowed to warm to room temperature and maintained at room temperature for a period of 24 hours.

An additional quantity of "Jones Reagent" was added (25 ml) dropwise at 10° C. over a period of 30 minutes.

The reaction mass was stirred at room temperature for another 24 hours.

50 ml Diethyl ether is then added to the reaction mass and the organic layer is separated from the aqueous layer. The aqueous layer was washed with diethyl ether (two 25 ml volumes) and the combined ether layers were then washed with saturated sodium bicarbonate (two 50 ml portions) followed by water (two 25 ml portions) and followed by saturated sodium chloride solution (two 25 ml portions).

The organic layer was dried over anhydrous magnesium sulfate and evaporated to yield 3.0 grams of product.

FIG. 17 is the GLC profile for the crude reaction product of Example VI (Conditions: SE-30 column programmed at 80°-220° C. at 8° C. per minute). The peaks indicated by reference numerals 172 and 174 are for the compounds having the structures:

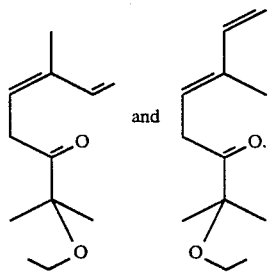

The peaks indicated by reference numerals 176 and 178 are for the compounds having the structures:

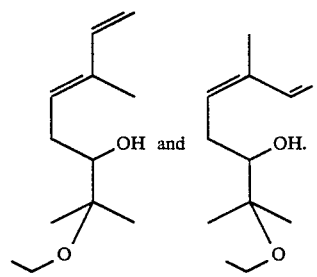

FIG. 18 is the NMR spectrum for the peaks indicated by reference numerals 172 and 174 of the GLC profile of FIG. 17 containing the compounds having the structures:

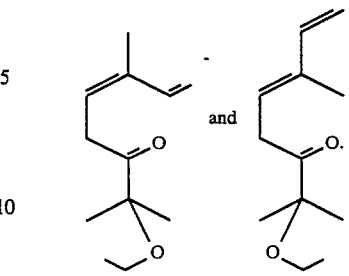

EXAMPLE VII

Reaction of Myroxide Using Para Toluene Sulfonic Acid, Water and Ethanol

Reaction:

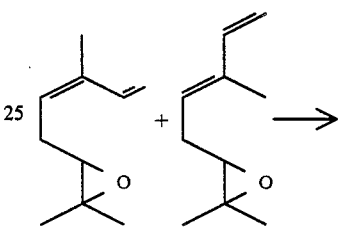

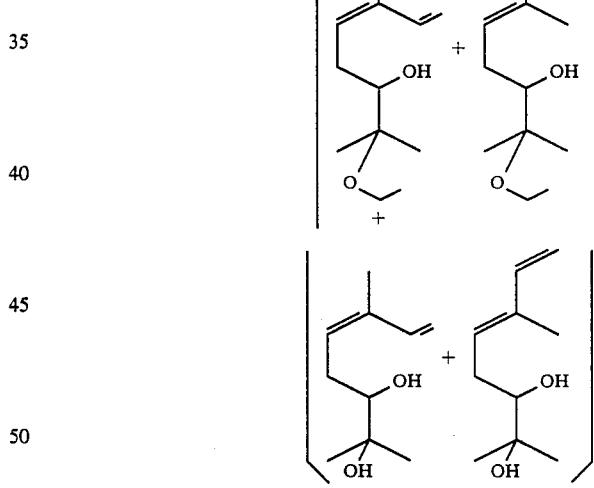

To a 125 ml reaction flask was added 45 ml food grade ethyl alcohol (5% water), 5 ml distilled water and 20 ml myroxide.

With stirring 0.3 grams of para toluene sulfonic acid monohydrate was added to the reaction mass and the reaction mass was stirred for a period of five hours at room temperature. After the five hour period, the reaction mass was transferred to a separatory funnel. Saturated sodium chloride solution (50 ml) and 50 ml diethyl ether was added and the organic layer was separated from the aqueous layer. The organic layer was washed with 4 volumes of saturated sodium chloride solution (50 ml portions) and then dried over anhydrous magnesium sulfate and filtered. The solvent was removed to yield 25.4 grams of crude product. This material was then distilled on a micro rush over column to yield 5 fractions as follows:

| Fraction No. | Vapor Temp. (°C.) | Liquid Temp. (°C.) | Vacuum mm/Hg. Pressure |
|---|---|---|---|
| 1 | 77/86 | 93/97 | 3.0/3.0 |
| 2 | 86 | 100 | 3.0 |
| 3 | 87 | 107 | 3.0 |
| 4 | 88 | 137 | 3.0 |
| 5 | 68 | 155 | 3.0. |

FIG. 21 is the GLC profile for the crude reaction product of Example VII (Conditions: Fused silica OV-1 column programmed at 60°-220° C. at 4° C. per minute). The peaks indicated by reference numerals 2100 and 2102 are for the compounds having the structures:

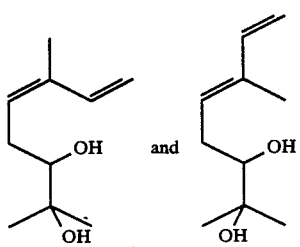

(ratio: 19:29). The peaks indicated by reference numerals 2104 and 2106 are for the compounds having the structures:

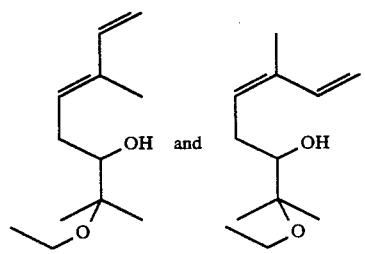

(ratio of percentages: 14%:21%).

EXAMPLE VIII

Reaction of Dihydro Myrcene Epoxide Using Para Toluene Sulfonic Acid

Reaction:

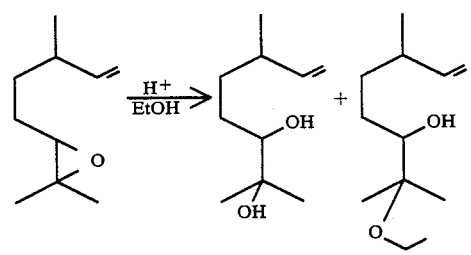

To a 50 ml reaction vessel equipped with magnetic stirrer was added 18 ml food grade ethyl alcohol (95% ethyl alcohol and 5% water), 2 ml distilled water and 4 grams of dihydro myrcene epoxide. With stirring 0.1 grams of para toluene sulfonic acid monohydrate was added and the mixture was stirred vigorously for a period of five hours. At the end of the five hour reaction time, the reaction mass was transferred to a separatory funnel and 50 ml saturated sodium chloride solution and 50 ml diethyl ether was added. The organic phase was separated from the aqueous phase and the organic phase was washed with four 20 ml portions of saturated sodium chloride solution. The organic extract was dried over anhydrous magnesium sulfate, filtered and the solvent recovered to yield 3.6 grams of crude reaction product. This material was then distilled on a micro rush over column to yield 5 fractions as follows:

| Fraction No. | Vapor Temp. (° C.) | Liquid Temp. (° C.) | Vacuum mm/Hg. Pressure |
|---|---|---|---|
| 1 | 53/55 | 77/77 | 3.0/3.0 |
| 2 | 57 | 79 | 3.0 |
| 3 | 63 | 85 | 3.0 |
| 4 | 66 | 120 | 3.0 |
| 5 | 66 | 185 | 3.0. |

FIG. 22 is the GLC profile for the crude reaction product of Example VIII containing the compounds having the structures:

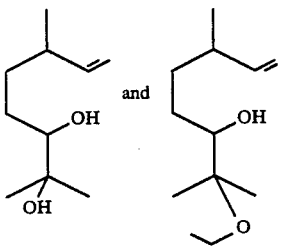

(Conditions: 50M×0.32 mm OV-1 fused silica column programmed at 60°-220° C. at 4° C. per minute).

FIG. 23 is the NMR spectrum for the compound having the structure:

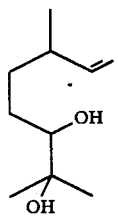

prepared according to Example VIII.

FIG. 24 is the NMR spectrum for the compound having the structure:

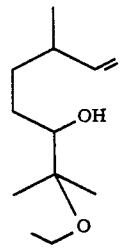

prepared according to Example VIII.

EXAMPLE IX

Reduction of Marigold Bifunctionals

Reaction:

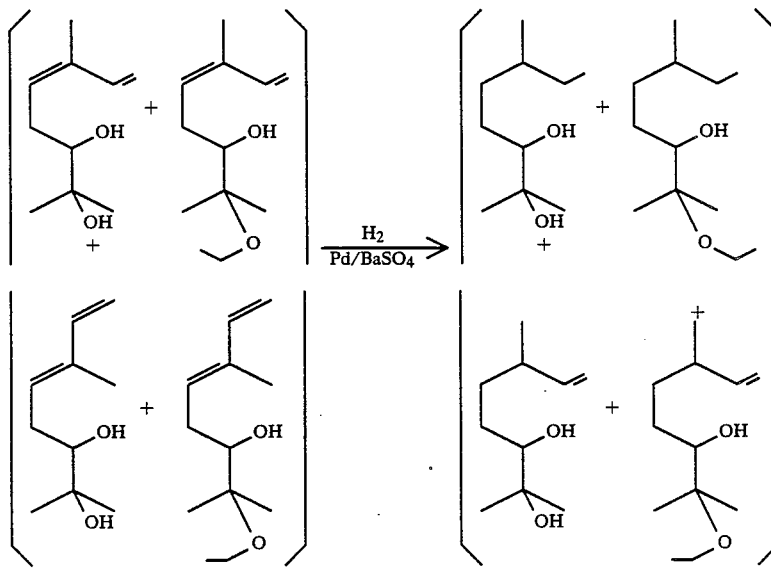

Into a 100 ml micro reaction flask 1.0 grams of the mixture of compounds having the structures:

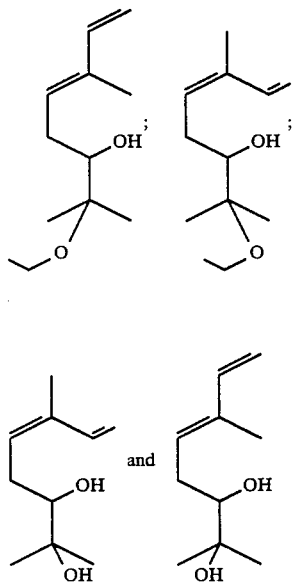

prepared according to Example IV was admixed with 10 ml isopropyl alcohol and 50 ml of 5% palladium on barium sulfate catalyst.

Hydrogen was bubbled into the reaction vessel with vigorous stirring until no more hydrogen was taken up by the reaction mass. The hydrogen taken up by the reaction mass was approximately 278.5 ml.

The reaction mass was filtered and centrifuged to remove catalyst and the isopropyl alcohol was then evaporated therefrom.

The resulting material was distilled using a micro still whereby 4 fractions were obtained. Analysis by means of NMR and IR analyses yielded the information that the following compounds were produced:

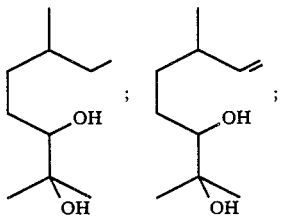

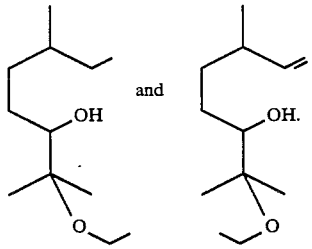

EXAMPLE X

Pine Fragrance

The following pine fragrance formulations are prepared:

| Ingredients | Parts By Weight EXAMPLES | | |
|---|---|---|---|
| | X(A) | X(B) | X(C) |
| Isobornyl acetate | 100 | 100 | 100 |
| Camphor | 10 | 10 | 10 |
| Terpineol | 25 | 25 | 25 |
| Fir balsam absolute (50%) in diethyl phthalate | 20 | 20 | 20 |
| Coumarin | 4 | 4 | 4 |
| Linalool | 30 | 30 | 30 |
| Frechyl alcohol | 10 | 10 | 10 |
| Anethol | 12 | 12 | 12 |
| Lemon terpenes washed | 50 | 50 | 50 |
| Borneol | 5 | 5 | 5 |
| Galbanum oil | 5 | 5 | 5 |

-continued

| Ingredients | Parts By Weight EXAMPLES | | |
|---|---|---|---|
| | X(A) | X(B) | X(C) |
| Turpentine Russian | 150 | 150 | 150 |
| Eucalyptol | 50 | 50 | 50 |
| 2,2,6-trimethyl-1-cyclo-hexene-1-carboxaldehyde | 12 | 12 | 12 |
| Maltol (1% in diethyl phthalate) | 5 | 5 | 5 |
| Mixture of compounds having the structures: | 28 | 0 | 0 |

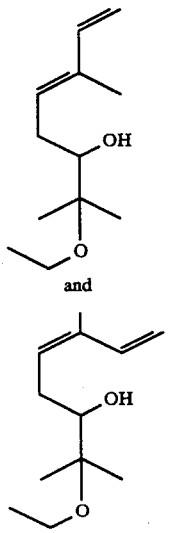

and prepared according to Example III.

| Mixture of compounds having the structures: | 0 | 28 | 0 |
|---|---|---|---|

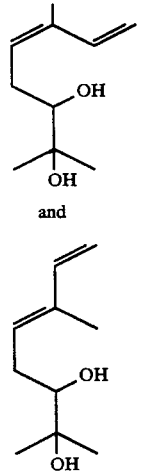

and

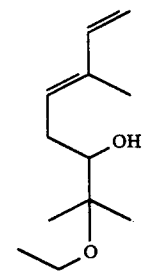

prepared according to Example V(B).

| Mixtures of compounds having the structures: | 0 | 0 | 28 |
|---|---|---|---|

-continued

| Ingredients | Parts By Weight EXAMPLES | | |
|---|---|---|---|
| | X(A) | X(B) | X(C) | and prepared according to Example VII.

The mixtures of compounds having the structures:

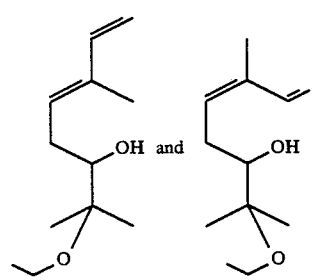

prepared according to Example III imparts to the pine formulation an intense, herbaceous, cut geranium stem and green undertone and floral and citrusy topnotes. Accordingly, the pine formulation of Example X(A) can be described as "pinery, with intense, green, herbaceous and cut geranium stem undertones and floral and citrusy" topnotes.

The mixtures of compounds having the structures:

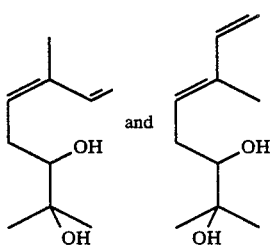

prepared according to Example V(B) imparts to the pine formulation of Example X(B) floral, fresh fruity, green and herbaceous undertones with floral and citrus topnotes. Accordingly, the pine formulation of Example X(B) can be described as "piney, with intense floral, fresh fruity, green and herbaceous undertones and floral and citrus topnotes".

The mixture of compounds having the structures:

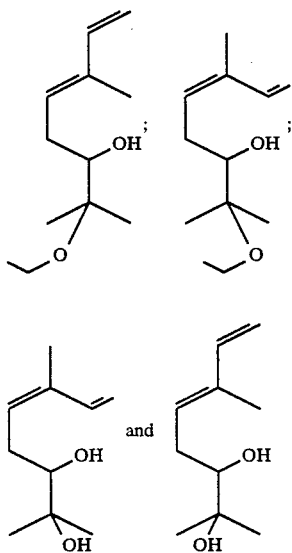

prepared according to Example VII imparts to the pine formulation of Example X(C) natural green, leafy, fruity, melony, peppery and citrusy undertones. Accordingly, the pine formulation of Example X can be described as "piney, with intense, natural green, leafy, fruity, melony, peppery and citrusy undertones".

EXAMPLE XI

Preparation of Cosmetic Powder Compositions

Cosmetic powder compositions are prepared by mixing in a ball mill 100 grams of talcum powder with 0.25 grams of each of the substances set forth in Table IV below. Each of the cosmetic powder compositions has an excellent aroma as described in Table IV below:

TABLE IV

| SUBSTANCE | AROMA DESCRIPTION |
| --- | --- |
| Mixture of compounds having the structures: | A green, herbaceous and cut geranium stem aroma profile with floral and citrusy topnotes. |

TABLE IV-continued

| SUBSTANCE | AROMA DESCRIPTION |
| --- | --- |
| prepared according to Example III. | |
| Mixture of compounds having the structures: prepared according to Example V(B). | A floral, fresh fruity, green and herbaceous aroma profile with floral and citrusy topnotes. |
| Mixture of compounds having the structures: | A natural green and leafy aroma profile with fruity, melony, |

TABLE IV-continued

| SUBSTANCE | AROMA DESCRIPTION |
|---|---|
| 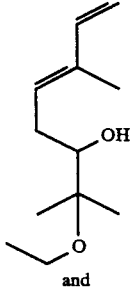 and 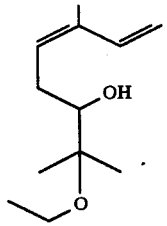 prepared according to Example V(C). | peppery and citrusy undertones. |
| The mixture of compounds having the structures: 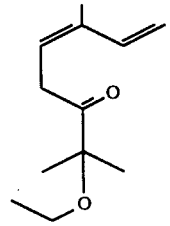 and 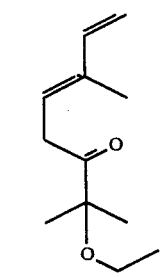 prepared according to Example VI. | An intense highly substantive tagette aroma profile. |
| Mixture of compounds having the structures: 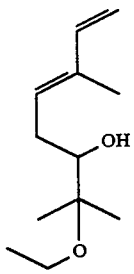 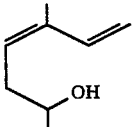 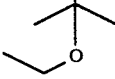 and 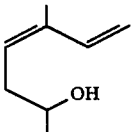 prepared according to Example VII. | A natural green and leafy aroma profile with fruity, melony, peppery and citrusy undertones. |
| Perfume composition of Example X(A). | Piney, with intense, green, herbaceous and cut geranium stem undertones and floral and citrusy topnotes. |
| Perfume composition of Example X(B). | Piney, with intense floral, fresh fruity, green and herbaceous undertones and floral and citrous topnotes. |
| Perfume composition of Example X(C). | Piney, with intense, natural green, leafy, fruity, melony, peppery and citrusy undertones. |

EXAMPLE XII

Perfume Liquid Detergent

Concentrated liquid detergents with aromas as set forth in Table IV of Example XI (which detergents are prepared from Lysine salt of n-dodecyl benzene sulfonic acid as more specifically described in U.S. Pat. Ser. No. 3,948,818 issued on Apr. 6, 1976, the specification for which is incorporated by reference herein) are prepared containing each of the substances set forth in Table IV of Example XI, supra. They are prepared by adding and homogeneously mixing the appropriate quantity of perfumery subtance as set forth in Table IV of Example XI in the liquid detergent. The detergents all possess aromas as set forth in Table IV of Example XI, the intensity increasing with greater concentrations of perfumery substance of Table IV of Example XI, supra.

EXAMPLE XIII

Preparation of a Cologne and Handkerchief Perfume

The perfume substances of Table IV of Example XI, supra, are incorporated into colognes at concentrations of 1.5%, 2.0%, 2.5%, 3.0% and 4.0% in 80% and 90% aqueous ethanol; and into a handkerchief perfume composition at concentrations of 10%, 15%, 20%, 25% and 30% (in 85%, 90% and 95% aqueous ethanol). Distinct and definitive aromas as set forth in Table IV of Example XI are imparted to the cologne and to the handkerchief perfume compositions.

EXAMPLE XIV

Preparation of a Detergent Composition

A total of 100 grams of a detergent powder ( a non-ionic detergent powder containing a proteolytic enzyme prepared according to Example I of Canadian Letters Patent No. 985,190 issued on Mar. 9, 1976, disclosure of which is incorporated by reference herein) is mixed with 0.15 grams of each of the substances set forth in Table IV of Example XI, supra, until substantially homogeneous compositions are obtained. These compositions have excellent aromas as set forth in Table IV of Example XI.

EXAMPLE XV

Preparation of Soap

Each of the perfumery substances of Table IV of Example XI are incorporated into soap (LVU-1) at 0.1% by weight of each substance. After two weeks in the oven at 90° F., each of the soaps showed no visual effect from the heat. Each of the soaps manifested an excellent aroma as set forth in Table IV of Example XI, supra.

EXAMPLE XVI

Preparation of Soap Composition

One hundred grams of soap chips (IVORY ®, registered trademark of the Proctor & Gamble Co. of Cincinnati, Ohio.) are mixed individually with one gram each of the perfumery sustances of Table IV of Example XI, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table IV of Example XI, supra.

EXAMPLE XVII

Preparation of a Solid Detergent Composition

A detergent is prepared from the following ingredients according to Example I of Canadian Letters Patent No. 1,007,948, the specification for which is incorporated by reference herein:

| Ingredients | Parts by Weight |
|---|---|
| "NEODOL ® 45-II (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume sustances of Table IV of Example XI, supra. The detergent samples each have excellent aromas as set forth in Table IV of Example XI, supra.

EXAMPLE XVIII

Utilizing the procedure of Example I at column 15 of U.S. Pat. No. 3,632,396 (the specification for which is incorporated by reference herein), a non-woven cloth substrate useful as a drier-added fabric softening article of manufacture is prepared, wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.);
   57 percent $C_{20-22}$HAPS
   22 percent isopropyl alcohol
   20 percent antistatic agent
   1 percent of one of the perfume substances of Table IV of Example XI.

A fabric softening composition prepared as set forth above having the above aroma characteristics as set forth in Table IV of Example XI, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and an outer coating weight ratio of about 1:1 by weight of substrate. The aroma set forth in Table IV of Example XI is imparted in a pleasant manner to the headspace in the dryer on operation thereof, using said drier-added fabric softening nonwoven fabric.

What is claimed is:

1. A 3,7-dimethyl-6,7-dioxo-1,3-octadiene defined according to the structure:

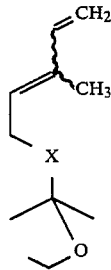

wherein X is a moiety selected from the group consisting of:

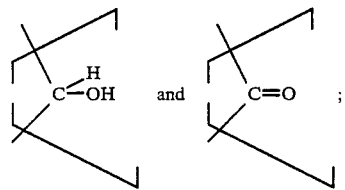

and wherein the wavy lines represent a "E" or "Z" configuration of the vinyl or methyl moieties about the 3,4-pi-bond.

2. A process for augmenting or enhancing the aroma of a perfume composition, perfumed article or cologne comprising the step of adding to said perfume composition, perfumed article or cologne, an aroma augmenting or enhancing quantity of at least one 3,7-dimethyl-6,7- dioxo-1,3-octadiene defined according to the structure:

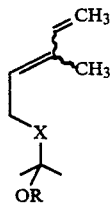

wherein R is selected from the group consisting of hydrogen and ethyl; wherein X is a moiety selected from the group consisting of:

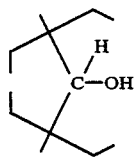

and

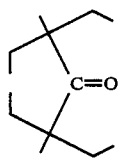

and wherein each of the wavy lines represents a "E" or "Z" configuration of the vinyl or methyl moieties about the 3,4-pi-bond.

3. A mixture of 3,7-dimethyl-6,7-dioxo-1,3-octadienes defined according to the structures:

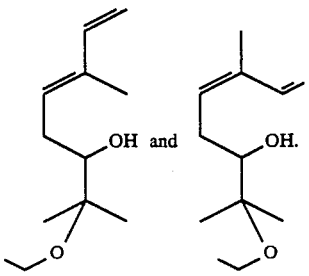

4. A mixture of 3,7-dimethyl-6,7-dioxo-1,3-octadienes defined according to the structures:

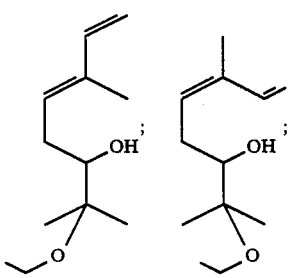

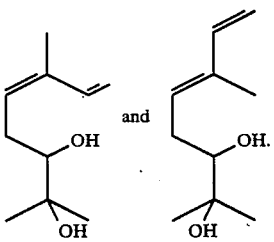

5. The process of augmenting or enhancing the aroma of a perfume composition, cologne or perfumed article comprising the step of intimately admixing with said perfume composition, cologne or perfumed article, an aroma augmenting or enhancing quantity of the product of claim 4.

6. A process for augmenting or enhancing the aroma of a perfume composition, cologne or perfumed article comprising the step of intimately admixing with said perfume composition, cologne or perfumed article, an aroma augmenting or enhancing quantity of a mixture of 3,7-dimethyl-6,7-dioxo-1,3-octadienes defined according to the structures:

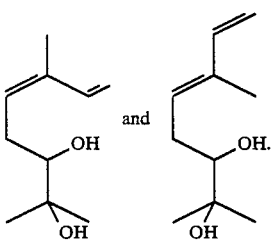

* * * * *